United States Patent
Fahmy et al.

(10) Patent No.: US 9,739,771 B2
(45) Date of Patent: Aug. 22, 2017

(54) PHYSIOLOGIC SAMPLE PREPARATION FOR NANOSENSORS

(75) Inventors: Tarek M. Fahmy, New Haven, CT (US); Eric D. Stern, Cambridge, MA (US); Mark A. Reed, Monroe, CT (US)

(73) Assignee: YALE UNIVERSITY, New Haven, CT (US)

( * ) Notice: Subject to any disclaimer, the term of this patent is extended or adjusted under 35 U.S.C. 154(b) by 1339 days.

(21) Appl. No.: 13/218,846

(22) Filed: Aug. 26, 2011

(65) Prior Publication Data

US 2012/0107954 A1 May 3, 2012

Related U.S. Application Data

(63) Continuation of application No. PCT/US2010/025412, filed on Feb. 25, 2010.

(60) Provisional application No. 61/156,123, filed on Feb. 27, 2009, provisional application No. 61/172,831, filed on Apr. 27, 2009.

(51) Int. Cl.
G01N 33/566 (2006.01)
G01N 33/543 (2006.01)
B01L 3/00 (2006.01)
G01N 30/60 (2006.01)

(52) U.S. Cl.
CPC .. *G01N 33/54386* (2013.01); *B01L 3/502761* (2013.01); *B01L 2200/0652* (2013.01); *B01L 2300/0636* (2013.01); *B01L 2300/0816* (2013.01); *B01L 2300/0864* (2013.01); *B01L 2300/0896* (2013.01); *B01L 2400/086* (2013.01); *G01N 30/6095* (2013.01)

(58) Field of Classification Search
None
See application file for complete search history.

(56) References Cited

U.S. PATENT DOCUMENTS

| | | | | |
|---|---|---|---|---|
| 5,986,076 A * | 11/1999 | Rothschild | ............ | C07H 19/04 424/130.1 |
| 6,074,827 A * | 6/2000 | Nelson | ................ | G01N 33/569 435/6.1 |
| 6,440,725 B1 * | 8/2002 | Pourahmadi | ...... | B01L 3/502715 422/547 |
| 2005/0079520 A1 * | 4/2005 | Wu | ...................... | C12Q 1/6804 435/6.18 |
| 2007/0253976 A1 | 11/2007 | Paterson et al. | | |
| 2008/0032417 A1 | 2/2008 | Olejnik et al. | | |
| 2008/0220982 A1 | 9/2008 | Vu | | |
| 2009/0053732 A1 | 2/2009 | Vermesh et al. | | |
| 2009/0066348 A1 * | 3/2009 | Shin | ........................ | G09B 7/08 324/693 |
| 2009/0124025 A1 * | 5/2009 | Hamilton | ............... | B82Y 15/00 436/524 |
| 2009/0264298 A1 * | 10/2009 | Lim | ................... | C12N 15/1062 506/1 |
| 2010/0196934 A1 * | 8/2010 | Peretz | ................ | G01N 33/6896 435/7.92 |
| 2010/0311188 A1 * | 12/2010 | Nazareth | .............. | G01N 33/559 436/501 |

FOREIGN PATENT DOCUMENTS

WO 2008/121691 10/2008

OTHER PUBLICATIONS

Kolmakov et al., "Chemical Sensing and Catalysts by One-Dimensional Metal-Oxide Nanostructures," 2004, *Annu. Rev. Mater. Res.*, 34:151-180.
McLaren, "Sus scrofa chromosome 11 clone CH242-137E14, Working Draft Sequence, 3 unordered pieces," GenBank: CT956077.2, 2008 [Retrieved from the Internet on Jul. 2, 2010; http://www.ncbi.nim.nih.gov/sites/entrez?db—nuccore &itool=toolbar].

* cited by examiner

*Primary Examiner* — Ann Lam
(74) *Attorney, Agent, or Firm* — Pabst Patent Group LLP

(57) ABSTRACT

The present invention provides a microfluidic purification chip for capturing a biomarker from a physiological solution. The present invention also provides a method of capturing and releasing a biomarker, wherein the biomarker is originally in a physiological solution. The present invention further provides a method of pre-purifying and measuring the concentration of a biomarker in a physiological solution.

11 Claims, 28 Drawing Sheets

1. Cap-Rel Chip
2. Housing/Tubing
3. Nanosensors
4. Valve
5. Photocleavable
6. 1" Anti-PSA
7. 1" Anti-CA15.3
8. 2" Anti-PSA
9. 2" Anti-CA15.3
10. PSA
11. CA15.3
12. Spiked blood
13. Buffer

SEQUENCE LISTING

<160> NUMBER OF SEQ ID NOS: 4

<210> SEQ ID NO 1
<211> LENGTH: 238
<212> TYPE: PRT
<213> ORGANISM: Homo sapiens

<400> SEQUENCE: 1

```
Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
        50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
                100                 105                 110

Pro Gly Asp Asp Ser Ser His Asp Leu Met Leu Leu Arg Leu Ser Glu
            115                 120                 125

Pro Ala Glu Leu Thr Asp Ala Val Lys Val Met Asp Leu Pro Thr Gln
        130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
                180                 185                 190

Thr Lys Phe Met Leu Cys Ala Gly Arg Trp Thr Gly Gly Lys Ser Thr
            195                 200                 205

Cys Ser Trp Val Ile Leu Ile Thr Glu Leu Thr Met Pro Ala Leu Pro
        210                 215                 220

Met Val Leu His Gly Ser Leu Val Pro Trp Arg Gly Val
225                 230                 235
```

<210> SEQ ID NO 2
<211> LENGTH: 96
<212> TYPE: PRT
<213> ORGANISM: Homo sapiens

<400> SEQUENCE: 2

```
Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Ile Pro Ala Pro Thr Thr Thr Lys Ser Cys Arg
        50                  55                  60

Glu Thr Phe Leu Lys Cys Phe Cys Arg Phe Ile Asn Lys Gly Val Phe
65                  70                  75                  80

Trp Ala Ser Pro Ile Leu Ser Ser Gly Gln Asp Leu Trp Trp Tyr Asn
```

```
<210> SEQ ID NO 3
<211> LENGTH: 20
<212> TYPE: DNA
<213> ORGANISM: Artificial Sequence
<220> FEATURE:
<223> OTHER INFORMATION: synthetically prepared

<400> SEQUENCE: 3
cgtagaggtt cagttgcagc                                               20

<210> SEQ ID NO 4
<211> LENGTH: 25
<212> TYPE: DNA
<213> ORGANISM: Artificial Sequence
<220> FEATURE:
<223> OTHER INFORMATION: synthetically prepared

<400> SEQUENCE: 4
gctgcaactg aacctctacg agtgc                                         25
```

PHYSIOLOGIC SAMPLE PREPARATION FOR NANOSENSORS

CROSS-REFERENCE TO RELATED APPLICATION

The present application is a continuation of and claims priority to International Application PCT/US2010/025412, filed Feb. 25, 2010, and published under PCT Article 21(2) in English, which claims priority to U.S. Provisional Applications No. 61/156,123, filed Feb. 27, 2009, and No. 61/172,831, filed Apr. 27, 2009, which applications are incorporated by reference herein in their entireties.

STATEMENT REGARDING FEDERALLY SPONSORED RESEARCH OR DEVELOPMENT

This invention was made with government support under Grant No. 5R01 HL085416, awarded by the National Institutes of Health. The U.S. Government therefore has certain rights in this invention.

BACKGROUND OF THE INVENTION

A biomarker is a term used to refer to a biomolecule or cell that may be measured in the blood or tissue of an individual, and which concentration reflects the presence or severity of a disease state in the individual. Biomarkers may be specific cells, molecules, genes, gene products, proteins, enzymes, or hormones. Complex organ functions or general characteristic changes in biological structures may also serve as biomarkers. A biomarker may be used as an indicator of the biological or metabolic state of an organism. More specifically, changes in the amounts of a biomarker in an individual may be correlated with the progression of a disease in the individual, the risk of the individual to develop a disease, or the susceptibility of a disease in the individual to a given treatment.

Biomarkers have emerged as potentially important diagnostic tools for cancer and many other diseases. Continuing discoveries of such biomarkers and their aggregation into molecular signatures suggests that multiple biomarkers may be necessary to precisely define disease states. Parallel detection of biomarker arrays is thus essential for translation from benchtop discovery to clinical validation. Such a technique would enable rapid, point-of-care applications requiring immediate diagnosis from a physiological sample. Critically, such a system should also be capable of detecting very low levels of aberrant genes and proteins, as many biomarkers are present at minute concentrations during early disease phases (Etzioni et al., 2003, Nature Rev. Cancer 3:243-252; Liang & Chan, 2007, Clin. Chim. Acta 381:93-97; Fan et al., 2008, Nature Biotechnol. 26:1373-1378; Zheng et al., 2005, Nature Biotechnol. 23:1294-1301). Given these requirements, the use of conventional diagnostic assays has been a limiting factor (Fan et al., 2008, Nature Biotechnol. 26:1373-1378; Zheng et al., 2005, Nature Biotechnol. 23:1294-1301; Nagrath et al., 2007, Nature 450:1235-1239). An approach that is based on rapid, label-free sensing technologies would be ideally suited for clinical applications (Zheng et al., 2005, Nature Biotechnol. 23:1294-1301; Cui et al., 2001, Science 293:1289-1292; Jain, 2005, Clin. Chim. Acta 358:37-54; Burg et al., 2007, Nature 446:1066-1069; Kim et al., 2007, Appl. Phys. Lett. 91:103901; Stern et al., 2007, Nature 445:519-522; Stern et al., 2008, IEEE Trans. Electron. Dev. 55:3119-3130; Bunimovich et al., 2006, J. Am. Chem. Soc. 128:16323-16331).

Since their introduction in 2001, label-free nanosensors have demonstrated great potential to serve as point-of-care detectors capable of ultrasensitive, real-time, multiplexed detection of multiple biomolecular species (Zheng et al., 2005, Nature Biotechnol. 23:1294-1301; Cui et al., 2001, Science 293:1289-1292; Jain, 2005, Clin. Chin Acta 358: 37-54; Burg et al., 2007, Nature 446:1066-1069; Kim et al., 2007, Appl. Phys. Lett. 91:103901; Stern et al., 2007, Nature 445:519-522; Stern et al., 2008, IEEE Trans. Electron. Dev. 55:3119-3130; Bunimovich et al., 2006, J. Am. Chem. Soc. 128:16323-16331). Despite their appeal, electronic nanosensors continue to be a challenge to implement, because fundamental limitations render them incapable of sensing molecules in complex, physiological solutions. Biofouling and non-specific binding readily degrade the minute active surface areas of such devices (<0.1 $\mu m^2$; Gupta et al., 2006, Proc. Natl. Acad. Sci. USA 103:13362-13367). Furthermore, label-free sensing requires purified, precisely controlled buffers to enable measurements to be performed. In the case of nanowire field-effect transistor (FET) sensing, low salt (<~1 mM) buffers are required to prevent screening of the charge-based electronic signal (Stern et al., 2008, IEEE Trans. Electron. Dev. 55:3119-3130; Stern et al., 2007, Nano Lett. 7:3405-3409). Because of these incompatibilities, label-free nanosensing has not been reported for complex, physiologic media, a critical step for translation of this technology to bedside applications.

There is thus a great need in identifying novel devices that may be used to purify biomarkers of interest before these biomarkers are analyzed by a nanosensor. These devices would allow the purification and concentration of biomarkers from biological samples, increasing the sensitivity of detection by the nanosensor and decreasing interference by the biofluid in which the biomarker is contained. The present invention fulfills this need.

SUMMARY OF THE INVENTION

In one aspect, the invention includes a microfluidic purification chip for capturing at least one biomarker from a physiological solution. The microfluidic purification chip comprises an immobilized first antibody directed to the at least one biomarker. The immobilized first antibody is attached to the microfluidic purification chip by a molecular crosslinker. The molecular crosslinker comprises a molecular spacer and a cleavable group.

In one embodiment, the at least one biomarker is PSA (SEQ ID NO:1) or CA15.3 (SEQ ID NO:2).

In one embodiment, the molecular spacer is selected from the group consisting of a peptide, a nucleic acid, a polyethylene glycol, and an alkylene group. In another embodiment, the molecular spacer is a nucleic acid. In yet another embodiment, the nucleic acid is a single-stranded DNA oligonucleotide. In yet another embodiment, the nucleic acid is 5'-CGT AGA GGT TCA GTT GCA GC-3' (SEQ ID NO:3).

In one embodiment, the cleavable group is a photocleavable group. In another embodiment, the group is 1-(4'-amino-2'-nitro-phenyl)ethyl.

In one embodiment, the molecular crosslinker further comprises a biotin-containing moiety. In another embodiment, the molecular crosslinker is Compound (I):

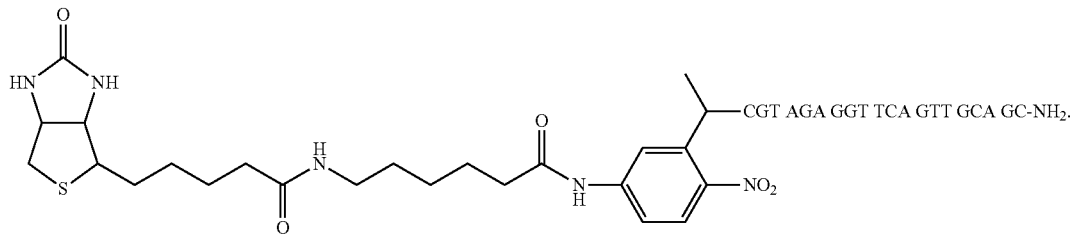

In yet another embodiment, the amino group in Compound (I) is coupled through an amide bond to a carboxylic acid of the first antibody. In yet another embodiment, the microfluidic purification chip is derivatized with avidin and the biotin-containing moiety of the molecular crosslinker binds to the avidin.

In one embodiment, the pillars in the microfluidic purification chip are about 100 μm in diameter. In another embodiment, the number of rows of the pillars ranges from about 25 to about 40. In yet another embodiment, the number of rows of the pillars is about 30. In yet another embodiment, the pillars in the microfluidic purification chip are arranged in a hexagonal geometry. In yet another embodiment, the width of the microfluidic purification chip ranges from about 2 mm to about 6 mm. In yet another embodiment, the width of the microfluidic purification chip is about 4 mm. In yet another embodiment, the length of the microfluidic purification chip ranges from about 5 mm to about 10 mm. In yet another embodiment, the length of the microfluidic purification chip is about 7 mm. In yet another embodiment, the height of the microfluidic purification chip ranges from about 50 μm to about 200 μm. In yet another embodiment, the height of the microfluidic purification chip is about 100 μm in height.

In one embodiment, the microfluidic purification chip is connected by a duct to a sensing chip, whereby solution flows from the microfluidic purification chip to the sensing chip through the duct. The duct optionally comprises a valve. In another embodiment, the maximum volume of solution held in the microfluidic purification chip is about half of the maximum volume of solution held in the sensing chip. In yet another embodiment, the maximum volume of solution held in the microfluidic purification chip is about 5 μL.

In one embodiment, the sensing chip is derivatized with a second antibody directed to the at least one biomarker. In another embodiment, the sensing chip is a nanoribbon sensor. In yet another embodiment, the gate voltage ($V_G$) for the sensing chip ranges from about −2.5 V to about −6 V. In yet another embodiment, the gate voltage ($V_G$) for the sensing chip is about −5 V.

In another aspect, the invention includes a method of capturing and releasing at least one biomarker, wherein the at least one biomarker is originally in a physiological solution. The method comprises the step of contacting the physiological solution comprising the at least one biomarker with a microfluidic purification chip, wherein the microfluidic purification chip comprises an immobilized first antibody directed to the at least one biomarker. The immobilized first antibody is attached to said microfluidic purification chip by a molecular crosslinker, and the molecular crosslinker comprises a molecular spacer and a cleavable group. The method further comprises removing the physiological solution from the microfluidic purification chip. The method further comprises optionally washing the microfluidic purification chip with a buffer. The method further comprises cleaving the cleavable group in a sensing buffer, to generate a biomarker-containing solution.

In one embodiment, the at least one biomarker is PSA (SEQ ID NO:1) or CA15.3 (SEQ ID NO:2).

In one embodiment, the molecular spacer is selected from the group consisting of a peptide, a nucleic acid, a polyethylene glycol, and an alkylene group. In another embodiment, the molecular spacer is a nucleic acid. In yet another embodiment, the nucleic acid is a single-stranded DNA oligonucleotide. In yet another embodiment, the nucleic acid is 5'-CGT AGA GGT TCA GTT GCA GC-3' (SEQ ID NO:1).

In one embodiment, the cleavage is performed with UV or visible light and the cleavable group is a photocleavable group. In another embodiment, the photocleavable group is 1-(4'-amino-2'-nitro-phenyl)ethyl.

In one embodiment, the molecular crosslinker further comprises a biotin-containing moiety. In another embodiment, the molecular crosslinker is Compound (I):

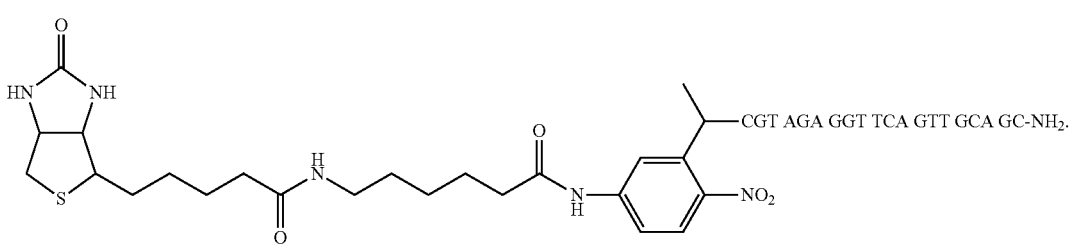

In yet another embodiment, the primary amino group in Compound (I) is coupled through an amide bond to a carboxylic acid of the first antibody. In yet another embodiment, the microfluidic purification chip is derivatized with avidin and the biotin-containing moiety of said molecular crosslinker binds to the avidin.

In one embodiment, the pillars in the microfluidic purification chip are about 100 μm in diameter. In another embodiment, the number of rows of pillars in the microfluidic purification chip ranges from about 25 to about 40. In yet another embodiment, the pillars in the microfluidic purification chip are arranged in a hexagonal geometry. In yet another embodiment, the width of the microfluidic purification chip is about 4 mm. In yet another embodiment, the length of the microfluidic purification chip is about 7 mm. In another embodiment, the height of the microfluidic purification chip is about 100 µm.

In yet another aspect, the invention includes a method of pre-purifying and measuring the concentration of at least one biomarker in a physiological solution. The method comprises the step of contacting the physiological solution comprising the at least one biomarker with a microfluidic purification chip, wherein the microfluidic purification chip comprises an immobilized first antibody directed to the at least one biomarker. The immobilized first antibody is attached to the microfluidic purification chip by a molecular crosslinker, and the molecular crosslinker comprises a molecular spacer and a cleavable group. The method further comprises the step of removing the physiological solution from the microfluidic purification chip. The method further comprises the step of optionally washing the microfluidic purification chip with a buffer. The method further comprises the step of cleaving the cleavable group in a sensing buffer, to generate a biomarker-containing solution. The method further comprises the step of transferring the biomarker-containing solution to a sensing chip, wherein the sensing chip is derivatized with a second antibody directed to the at least one biomarker. The method further comprises the step of contacting the biomarker-containing solution with the sensing chip. The method further comprises the step of determining concentration of the biomarker in the biomarker-containing solution. The method further comprises the step of determining concentration of the biomarker in the physiological solution.

In one embodiment, the at least one biomarker is PSA (SEQ ID NO:1) or CA15.3 (SEQ ID NO:2).

In one embodiment, the microfluidic purification chip is connected to the sensing chip by a duct, wherein the duct is used to transfer said biomarker-containing solution from the microfluidic purification chip to the sensing chip. The duct optionally comprises a valve. In another embodiment, the maximum volume of solution held in the microfluidic purification chip is about half of the maximum volume of solution held in the sensing chip. In yet another embodiment, the maximum volume of solution held in the microfluidic purification chip is about 5 µL. In yet another embodiment, the sensing chip is a nanoribbon sensor. In yet another embodiment, the gate voltage ($V_G$) for the sensing chip ranges from about −2.5 V to about −6 V. In yet another embodiment, the gate voltage ($V_G$) for the sensing chip is about −5 V. In yet another embodiment, the sensing solution has a Debye screening length of about $\lambda_D$=9.6 nm. In yet another embodiment, the sensing solution is 1 mM bicarbonate buffer.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIG. 1A illustrates first antibodies to multiple biomarkers (in a non-limiting example, prostate specific antigen—PSA—and carbohydrate antigen-15.3-CA15.3) bound with a photocleavable crosslinker to the microfluidic purification chip. The chip is contained in a plastic housing and a valve directs flow exiting the chip to either a waste receptacle or the nanosensor chip. In FIG. 1B, whole blood is injected into the chip with the valve set to the waste compartment (arrows indicates direction of fluid flow) and, if present in the sample, biomarkers bind their cognate antibodies. In FIG. 1C, washing steps follow blood flow, and the chip volume (5 µL) is filled with sensing buffer prior to UV irradiation, which cleaves the photolabile crosslinker and releases the antibody-antigen complexes into solution. In FIG. 1D, the valve is set to the nanosensor reservoir (arrow indicates direction of fluid flow) and the 5 µL volume is transferred to the nanosensor reservoir, enabling label-free sensing to be performed to determine the presence of specific biomarkers.

FIG. 2, comprising FIG. 2A illustrates the velocity profile, in term of streamlines, for a flow rate of 10 µL/min. FIG. 2B illustrates the velocity profile, in term of velocities, for a flow rate of 10 µL/min. FIG. 2C illustrates the PSA retention for a flow rate of 10 µL/min. FIG. 2D illustrates the PSA retention for a flow rate of 1 µL/min.

FIG. 3, comprising FIG. 3A illustrates the molecular structure of a photocleavable crosslinker contemplated within the invention. First-antibody conjugation was performed with the amino group (right) and binding to chip-bound avidin occurred through the biotin group (left). FIG. 3B illustrates the scanning electron micrograph of a representative width=4 mm, length=7 mm, height=100 µm capture-release (cap-rel) chip. The inset is an optical image of microfluidic purification chip operation during washing. FIG. 3C is a schematic representation of PSA and CA 15.3 detection using a modified ELISA technique. FIG. 3D illustrates the fluorescence optical micrograph of an anti-OVA functionalized microfluidic purification chip following OVA-FITC-spiked whole blood flow and washing. The inset plots the pixel intensity (iii) (determined by ImageJ) versus position for the cut line (shown as a broken line) (i) and similar cutlines from images of post-UV irradiation and transfer (ii) and of an anti-PSA functionalized microfluidic purification chip following OVA-FITC-spiked blood flow and washing. The same exposure times were used for all images. FIG. 3E is a scatter plot showing the concentration of PSA released from the capture-release (cap-rel) chip versus the concentration of PSA introduced in whole blood. FIG. 3F is a scatter plot showing the concentration of CA15.3 released from the capture-release (cap-rel) chip versus the concentration of CA15.3 introduced in whole blood. For FIGS. 3E and 3F, each datapoint represents the average of three separate microfluidic purification chip runs and error bars represent one standard deviation.

FIG. 8, comprising FIG. 8C illustrates the expansion of the region encompassed by the broken line box in FIG. 8B. FIG. 8D illustrates the expansion of the region encompassed by the broken line box in FIG. 8C.

FIG. 9, comprising FIG. 9A is an optical image of devices outfitted with sensing reservoirs. The inset shows an optical micrograph of a completed device. Only the central region of the device (black arrow) is exposed to the solution. Metal leads contact the device source and drain and fan out to larger contacts (not shown). The 25 nm thick silicon device appears light gray. FIG. 9B is a $I_{DS}$ ($V_{DS}$) graph for $V_G$ varied from 0 to −20V (arrow shows direction of increasing negative $V_G$) for a representative device illustrating p-type accumulation mode behavior. FIG. 9C is a $I_{DS}$ ($V_G$) plot ($V_{DS}$=1 V) for the device used in FIG. 9B. The inset highlights $I_{DS}$ (nA) around the operating point ($V_G$=−5V). FIG. 9D is a plot demonstrating the effect of varying solution gate voltage ($V_{G,SOLN}$) on device current ($I_{DS}$, solid line) and device-to-solution leakage current ($I_{LEAK}$, broken line) for $V_{DS}$=1 V.

FIG. 10, comprising FIG. 10A illustrates the anti-PSA functionalized device backgating (using the handle wafer). FIG. 10B illustrates the anti-CA15.3 functionalized device backgating (using the handle wafer). FIG. 10C illustrates the solution gating.

FIG. 11, comprising FIG. 11A illustrates the correlation of $I_{DS}$ and $V_{DS}$ post-APTS functionalization. FIG. 11B illustrates the correlation of $I_{DS}$ and $V_G$ post-APTS functionalization. FIG. 11C illustrates the correlation of $I_{DS}$ and $V_{DS}$ after complete functionalization and FBS blocking. FIG. 11D illustrates the correlation of $I_{DS}$ and $V_G$ after complete functionalization and FBS blocking.

FIG. 12, comprising

FIG. 13, comprising FIG. 13A illustrates the absolute sensor response (not normalized) of anti-PSA functionalized device to the spiked buffer solution (top trace) or to the microfluidic purification chip-purified sensing experiments (bottom trace), as displayed in FIGS. 14A-14B. FIG. 13B illustrates the absolute sensor response (not normalized) of anti-CA15.3 functionalized device to the spiked buffer solution (top trace) or to the microfluidic purification chip-purified sensing experiments (bottom trace), as displayed in FIGS. 14A-14B. FIG. 13C illustrates the absolute sensor response for the unspiked control blood sample for the anti-PSA functionalize device, as displayed in FIGS. 14A-14B. FIG. 13D illustrates the absolute sensor response for the unspiked control blood sample for the anti-CA15.3 functionalize device, as displayed in FIGS. 14A-14B. FIG. 13E illustrates the absolute sensor response for the microfluidic purification chip-purified PSA-spiked blood sample for the anti-PSA functionalize device, as displayed in FIGS. 14C-D. FIG. 13F illustrates the absolute sensor response for the microfluidic purification chip-purified CA15.3-spiked blood sample for the anti-CA15.3 functionalize device, as displayed in FIGS. 14C-D.

FIG. 14, comprising FIG. 14A illustrates response of an anti-PSA functionalized sensor to a microfluidic purification chip-purified blood sample initially containing 2.5 ng/ml PSA (and also 30 U/ml CA15.3), marked as (ii), or a control sample containing neither, marked as (i). FIG. 14B illustrates response of an anti-CA15.3 functionalized sensor to a microfluidic purification chip-purified blood sample initially containing 30 U/ml CA15.3 (and also 2.5 ng/ml PSA), marked as (ii), or a control sample containing neither, marked as (i). FIGS. 14C and 14D illustrate the normalized response of two anti-PSA (FIG. 14C) and two anti-CA15.3 (FIG. 14D) functionalized devices to microfluidic purification chip-purified blood containing both PSA and CA15.3, with concentrations labeled. A least-squares fit is represented by a solid black line over the selected region (line endpoints).

DETAILED DESCRIPTION OF THE INVENTION

Figure 1A:
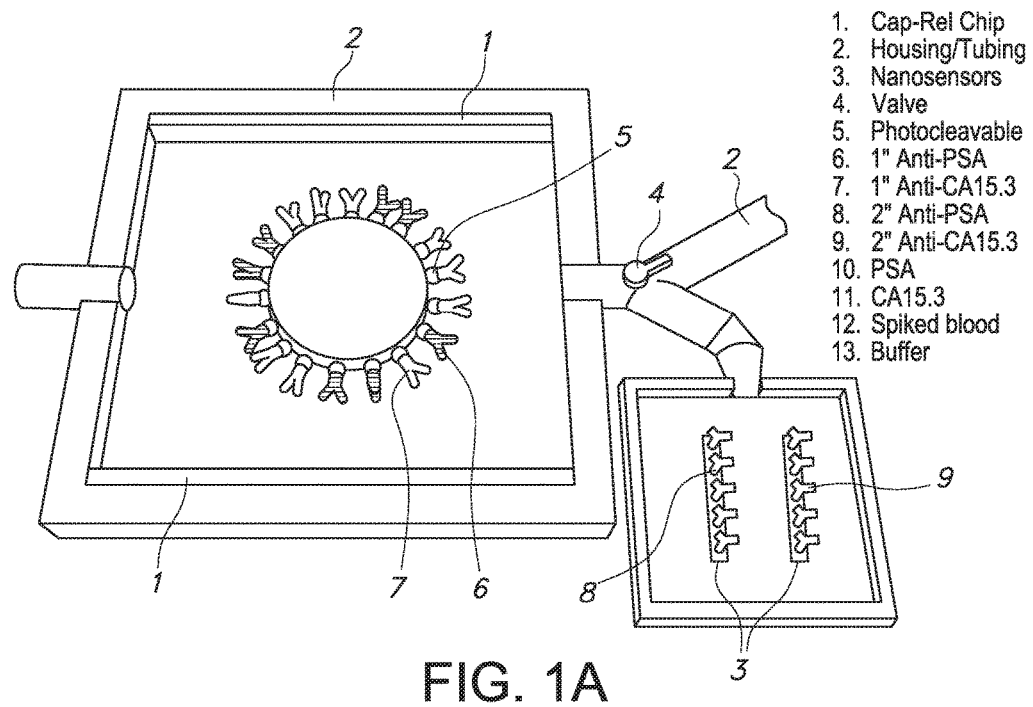
FIGS. 1A-1D, is a schematic illustration of the operation of a microfluidic purification chip.

The present invention relates to the discovery that a microfluidic purification chip may be used to pre-purify at least one biomarker of interest from a biological sample. This microfluidic purification chip captures at least one biomarker from a solution, such a physiological solution. After washing of the chip, the at least one biomarker may be released into a solution suitable for detection and quantitation of the biomarker.

In one aspect, the invention provides a microfluidic purification chip for capturing and releasing at least one biomarker from a biological sample. In another aspect, the invention provides a method of capturing and releasing at least one biomarker from a biological sample using a microfluidic purification chip. In yet another aspect, the invention provides a method of measuring the concentration of a biomarker in a physiological solution, using a microfluidic purification chip for capturing and releasing the biomarker.

Definitions

As used herein, each of the following terms has the meaning associated with it in this section.

As used herein, unless defined otherwise, all technical and scientific terms generally have the same meaning as commonly understood by one of ordinary skill in the art to which this invention belongs. Generally, the nomenclature used herein and the laboratory procedures in cell culture, molecular genetics, organic chemistry, and peptide chemistry are those well known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "physiological solution" refers to any solution comprising physiological material isolated from a living organism. Non-limiting examples of physiological materials contemplated within the invention are blood, blood subfractions, serum, lymphatic fluid, saliva, urine, sweat, vaginal fluid and sperm. In one embodiment, the physiological solution comprises material selected from the group consisting of blood, blood subfractions, serum, lymphatic fluid, saliva, urine, sweat, vaginal fluid and sperm. In another embodiment, the physiological solution comprises blood.

As used herein, PSA (SEQ ID NO:1) refers to prostate-specific antigen.

As used here, CA15.3 (SEQ ID NO:2) refers to Cancer Antigen 15-3.

As used herein, the term "polypeptide" refers to a polymer composed of amino acid residues, related naturally occurring structural variants, and synthetic non-naturally occurring analogs thereof linked via peptide bonds. Synthetic polypeptides may be synthesized, for example, using an automated polypeptide synthesizer. As used herein, the term "protein" typically refers to large polypeptides. As used herein, the term "peptide" typically refers to short polypeptides. Conventional notation is used herein to represent polypeptide sequences: the left-hand end of a polypeptide sequence is the amino-terminus, and the right-hand end of a polypeptide sequence is the carboxyl-terminus.

As used herein, the polypeptides include natural peptides, recombinant peptides, synthetic peptides or a combination thereof. A peptide that is not cyclic has an N-terminus and a C-terminus. The N-terminus has an amino group, which may be free (i.e., as a $NH_2$ group) or appropriately protected (for example, with a BOC or a Fmoc group). The C-terminus has a carboxylic group, which may be free (i.e., as a COOH group) or appropriately protected (for example, as a benzyl or a methyl ester). A cyclic peptide does not necessarily have free N- or C-termini, since they are covalently bonded through an amide bond to form the cyclic structure. The term "peptide bond" means a covalent amide linkage formed by loss of a molecule of water between the carboxyl group of one amino acid and the amino group of a second amino acid.

As used herein, amino acids are represented by the full name thereof, by the three letter code corresponding thereto, or by the one-letter code corresponding thereto, as indicated below:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, the term "antibody" refers to an immunoglobulin, whether natural or partly or wholly synthetically produced. The term also covers any polypeptide, protein or peptide having a binding domain that is, or is homologous to, an antibody binding domain. These may be isolated from natural sources, or may be partly or wholly synthetically produced. Examples of antibodies are intact immunoglobulin molecules, as well as fragments thereof, such as Fab, F(ab')2, Fv fragments, and single chain variable fragments (scFv), which are capable of binding an epitopic determinant. Antibody fragments refer to antigen-binding immunoglobulin peptides that are at least about 5 to about 15 amino acids or more in length, and that retain some biological activity or immunological activity of an immunoglobulin. Antibody as used herein includes polyclonal and monoclonal antibodies, hybrid, single chain, and humanized antibodies, as well as Fab fragments, including the products of a Fab or other immunoglobulin expression library, and suitable derivatives.

As used herein, the "first antibody" and the "second antibody" are distinct antibodies that are raised against the antigenic target of interest (for example, a protein, peptide, carbohydrate, nucleotide, deoxynucleotide, or other small molecule). The second antibody binds to a different biomarker epitope than the first antibody conjugated to the biotinylated-photocleavable crosslinker, and therefore binding of the primary antibody to the biomarker does not prevent binding of the secondary antibody to the biomarker. Antibodies that recognize and bind with high affinity and specificity to unique epitopes across a broad spectrum of biomolecules are available as high specificity monoclonal antibodies and/or as polyclonal antibodies. These antibodies are useful not only to detect specific biomolecules but also to measure changes in their level and specificity of modification by processes such as phosphorylation, methylation, or glycosylation.

As used herein, the term "specifically binds," referring to an antibody binding to a biomarker of choice, means that the antibody binds the biomarker of choice, or subunit thereof, but does not bind to a biological molecule that is not the biomarker of choice. Antibodies that specifically bind to an biomarker of choice, or subunit thereof, do not substantially cross-react with biological molecules outside the biomarker of choice.

As used herein, the term "monoclonal antibody" includes antibodies that display a single binding specificity and affinity for a particular epitope. These antibodies are mammalian-derived antibodies, including murine, human and humanized antibodies. As used herein, an "antibody heavy chain" refers to the larger of the two types of polypeptide chains present in all antibody molecules in their naturally occurring conformations. As used herein, an "antibody light chain" refers to the smaller of the two types of polypeptide chains present in all antibody molecules in their naturally occurring conformations.

As used herein, a "polynucleotide" means a single strand or parallel and anti-parallel strands of a nucleic acid. Thus, a polynucleotide may be either a single-stranded or a double-stranded nucleic acid.

As used herein, the term "nucleic acid" typically refers to large polynucleotides.

As used herein, the term "oligonucleotide" typically refers to short polynucleotides, which are generally not greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

As used herein, a "portion" of a polynucleotide means at least about twenty sequential nucleotide residues of the polynucleotide. It is understood that a portion of a polynucleotide may include every nucleotide residue of the polynucleotide.

As used herein, a "probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

As used herein, an "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

Microfluidic Purification Chip of the Invention

The invention includes a microfluidic purification chip, which captures at least one biomarker from an initial solution and then releases the at least one biomarker into a solution suitable for detection and quantitation. In one embodiment, the initial solution is a physiological solution. In another embodiment, the initial solution comprises blood.

The microfluidic purification chip may be prepared using techniques known to those skilled in the art. In a non-limiting example, the microfluidic purification chip may be prepared from silicon wafers according to the procedure illustrated in FIG. 4. In another non-limiting example, the microfluidic purification chip may be prepared from moldable plastic. In yet another non-limiting example, the microfluidic purification chip may have 3D flow, i.e., can be a matrix. Photoresist may be spun on the wafers and exposed using a mask. In one embodiment, the pillars used in this procedure are about 100 µm in diameter. The resist pattern may be transmitted to the oxide using reactive ion etching. Resist may be stripped by ashing and the silicon pillars may be realized with an etcher.

The dimensions of the microfluidic purification chip determine the volume of the solution that may be contained in the chip. In one embodiment, the width of the microfluidic purification chip ranges from about 2 mm to about 6 mm. In another embodiment, the microfluidic purification chip is about 4 mm in width. In yet another embodiment, the length of the microfluidic purification chip ranges from about 5 mm to about 10 mm. In yet another embodiment, the microfluidic purification chip is about 7 mm in length. In yet another embodiment, the height of the microfluidic purification chip ranges from about 50 µm to about 200 µm. In yet another embodiment, the microfluidic purification chip is about 100 µm in height. In yet another embodiment, the dimensions of the microfluidic purification chip are selected so that the maximum volume of solution contained in the microfluidic purification chip is about half that of the maximum volume of solution contained in the sensing chip. In yet another embodiment, the maximum volume of solution held in the microfluidic purification chip ranges from about 1 µL to about 10 µL. In yet another embodiment, the maximum volume of solution held in the microfluidic purification chip is about 1 µL. In yet another embodiment, the maximum volume of solution held in the microfluidic purification chip is about 5 µL. In yet another embodiment, the maximum volume of solution held in the microfluidic purification chip is about 10 µL.

The layout and arrangement of the pillars in the microfluidic purification chip may determine the efficacy of capture of the biomarker, as illustrated in FIG. 2. In one embodiment, the layout of the pillars in the microfluidic purification chip has a hexagonal geometry. In another embodiment, the layout of the pillars in the microfluidic purification chip has a triangular geometry. In yet another embodiment, the layout of the pillars in the microfluidic purification chip has a square geometry. In yet another embodiment, the number of pillar rows in the microfluidic purification chip ranges from about 10 to about 60. In yet another embodiment, the number of pillar rows in the microfluidic purification chip ranges from about 20 to about 60. In yet another embodiment, the number of pillar rows in the microfluidic purification chip ranges from about 20 to about 50. In yet another embodiment, the number of pillar rows in the microfluidic purification chip ranges from about 20 to about 40. In yet another embodiment, the number of pillar rows in the microfluidic purification chip ranges from about 25 to about 40. In yet another embodiment, the number of pillar rows in the microfluidic purification chip ranges from about 25 to about 35. In yet another embodiment, the number of pillar rows in the microfluidic purification chip is about 30.

As the biological fluid containing the biomarker flows through the chip, the biomarker may be captured in the microfluidic purification chip. The flow rate of the biological fluid may influence the efficiency of capture of the biomarker by the microfluidic purification chip. In one embodiment, the flow rate of biological fluid through the microfluidic purification chip ranges from about 0.1 µL/min to about 20 µL/min. In another embodiment, the flow rate of biological fluid through the microfluidic purification chip ranges from about 1 to about 15 µL/min. In yet another embodiment, the flow rate of biological fluid through the microfluidic purification chip ranges from about 5 µL/min to about 15 µL/min. In yet another embodiment, the flow rate of biological fluid through the microfluidic purification chip is about 1 µL/min. In yet another embodiment, the flow rate of biological fluid through the microfluidic purification chip is about 10 µL/min.

Preparation of First Antibody Conjugated to Molecular Crosslinker

The microfluidic purification chip may be derivatized with a first antibody directed to the biomarker of interest so that the immobilized first antibody may capture the biomarker of interest from the biological fluid. The immobilized first antibody may be attached to the surface of the microfluidic purification chip using any method known to those skilled in the art, provided that the immobilization method does not destroy the first antibody's ability to bind to the biomarker.

In one embodiment, the first antibody may be attached to the microfluidic purification chip by means of a molecular crosslinker. The molecular crosslinker comprises a molecular spacer and a cleavable group.

The cleavable group may be cleaved using a chemical reagent, such as an acid, a base, an oxidant or a reducer, or may be cleaved using a form of low-energy radiation, such as UV or visible radiation. In one embodiment, the cleavable group is a photocleavable crosslinker and may be cleaved using UV or visible radiation. In another embodiment, the photocleavable group is 1-(4'-amino-2'-nitro-phenyl)ethyl.

The molecular spacer may be any organic molecule capable of withstanding the immobilization and release of the biomarker without undergoing significant decomposition. The molecular spacer may be, for example, a peptide, a nucleic acid, a polyethylene glycol, or an alkylene group. In an embodiment, the molecular spacer is a single-stranded DNA oligonucleotide. In another embodiment, the single-stranded DNA oligonucleotide ranges in size from about 5 nucleotides to about 40 nucleotides. In yet another embodiment, the single-stranded DNA oligonucleotide ranges in size from about 10 nucleotides to about 30 nucleotides. In yet another embodiment, the single-stranded DNA oligonucleotide ranges in size from about 15 nucleotides to about 25 nucleotides. In yet another embodiment, the single-stranded DNA oligonucleotide is a 20-mer. In yet another embodiment, the single-stranded DNA oligonucleotide is 5'-CGT AGA GGT TCA GTT GCA GC-3' (SEQ ID NO:3).

The molecular spacer may be functionalized in at least two positions. In a non-limiting example, the molecular spacer is linear and the chemical functionalities are located on opposite extremities of the spacer. In one embodiment, at least one of the chemical functionalities is coupled with a cleavable group. In another embodiment, at least one of the chemical functionalities is coupled with a photocleavable group. In yet another embodiment, the 1-position of the 1-(4'-amino-2'-nitro-phenyl)ethyl photocleavable group is coupled to the molecular spacer. In yet another embodiment, the molecular spacer is a single-stranded DNA oligomer and the 1-position of 1-(4'-amino-2'-nitro-phenyl)ethyl is coupled to the 5'-terminus of the single-stranded DNA oligonucleotide.

The cleavable group may be further coupled to a biotin-coupled moiety. In one embodiment, the 4'-amino group of the 1-(4'-amino-2'-nitro-phenyl)ethyl photocleavable group is coupled to a biotin-containing moiety. In another embodiment, the molecular crosslinker is Compound (I):

molecular crosslinker has a carboxylic group and is conjugated via an amide bond to an accessible free amino group of the first antibody (from a lysine or arginine residue, for example). The amide bond formation may be performed using coupling agents such as 1-ethyl-3-(3-dimethylaminopropyl)-carbodiimide (EDC) and N-hydroxysulfosuccinimide (NHS) in an appropriate solvent, such as an aqueous buffer or an aqueous buffer comprising water-soluble organic solvents.

Functionalization of the Microfluidic Purification Chip with the First Antibody Conjugated to the Molecular Crosslinker The first antibody conjugated to the molecular crosslinker may be attached to the microfluidic purification chip through functional groups previously installed on the surface of the microfluidic purification chip. In one embodiment, the surface of the microfluidic purification chip is derivatized with a chemical group comprising avidin, and the molecular crosslinker conjugated to the first antibody comprises biotin.

In a non-limiting example, the microfluidic purification chip may be treated with a solution of a silane, such as 3-aminopropyltriethoxysilane, under an inert atmosphere, and then heated for a defined amount of time. This treatment leads to the reaction of the silane with the surface of the chip. The resulting amino groups attached to the surface of the chip may then be reacted with avidin in presence of coupling reagents such as EDC and sulfo-NHS. The derivatized chip may then be treated with a solution of fetal bovine serum (FBS) to block any unreacted site.

The derivatived chip may then be treated with the first antibody conjugated to the molecular crosslinker, whereupon the biotin and the avidin moieties bind to each other and the first antibody conjugated to the molecular crosslinker becomes attached to the microfluidic purification chip.

Operation of the Microfluidic Purification Chip

As the biological sample flows through the microfluidic purification chip functionalized with the first antibody conjugate, the biomarker of interest may bind to the first antibody. The sample may be kept in contact with the microfluidic purification chip for sufficient time to ensure appropriate binding between the biomarker and the immobilized first antibody. The extent of binding of the biomarker to the immobilized first antibody may be evaluated with any method known to those skilled in the art, such as the modified ELISA test described below.

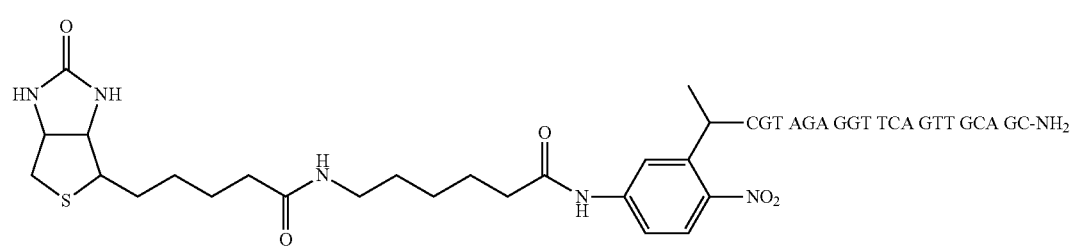

(I)

The molecular crosslinker may be conjugated to the first antibody, using any techniques known to those in the art, with the requirement that the conjugation does not destroy the antibody's ability to bind to the biomarker of interest. In one embodiment, the molecular crosslinker has a free amino group and is coupled via an amide bond to an accessible free carboxylic group of the first antibody (from an aspartate or glutamate residue, for example). In another embodiment, the Once the biomarker has had the opportunity to bind to the immobilized first antibody, the solution may be drained from the chip. Washing and sensing buffers may then be perfused through the device. In the case that the first antibody conjugate comprises a photolabile crosslinker, all operations should preferably be performed in dim light.

The microfluidic purification chip may then be charged with the buffer of choice, preferentially a buffer that does not interfere with subsequent sensing of the biomarker. In the case where the first antibody conjugate comprises a photolabile crosslinker, the captured biomarker may be released from the microfluidic purification chip by irradiating the chip with UV radiation. The length and intensity of the UV irradiation may be varied to optimize release of the captured biomarker and minimize any potential decomposition of the material. The amount of released biomarker obtained by this procedure may be evaluated by the modified ELISA test described below.

In one aspect, the microfluidic purification chip of the invention may be used for purifying the biomarker of interest from a physiological solution.

In another aspect, the microfluidic purification chip of the invention may be used for concentrating the biomarker of the interest from a physiological solution. In this case, the physiological solution may be contacted with the microfluidic purification chip of the invention, to ensure that the primary antibody immobilized on the microfluidic purification chip enters in contact with the biomarker in solution and has the opportunity to capture the biomarker. In one embodiment, efficient capture of the biomarker may be achieved by prolonged contact of the microfluidic purification chip with the physiological solution comprising the biomarker. In another embodiment, efficient capture of the biomarker may be achieved by multiple contact passes of the microfluidic purification chip with the physiological solution comprising the biomarker.

Figure 3A:
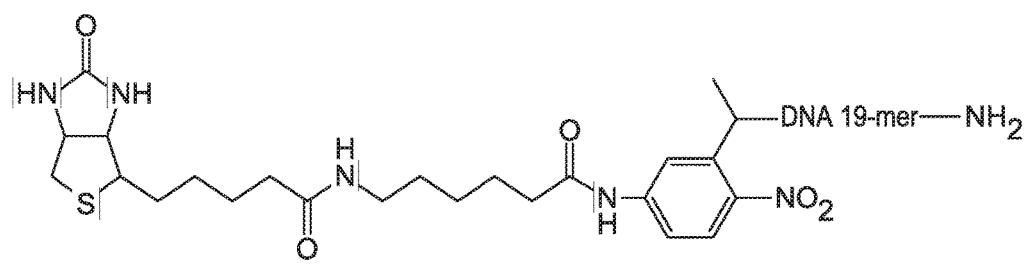
FIGS. 3A-F, is a series of images illustrating the operation of the microfluidic purification chip.
Figure 3B:
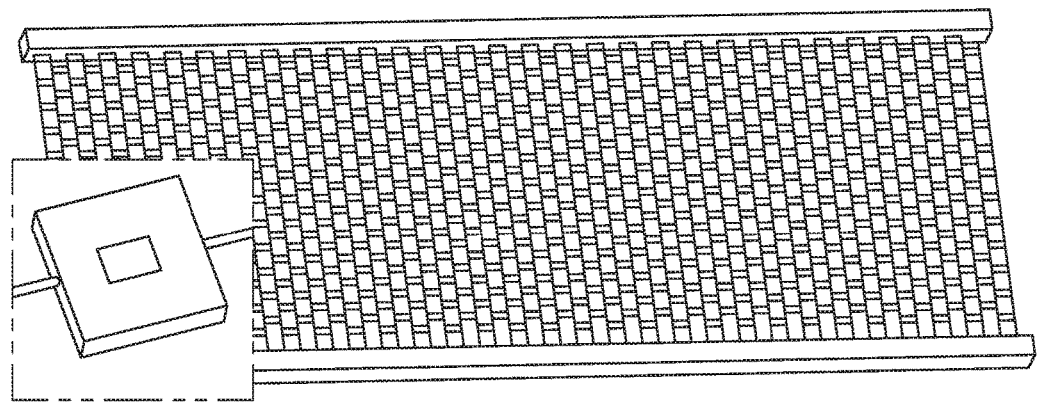
Figure 3C:
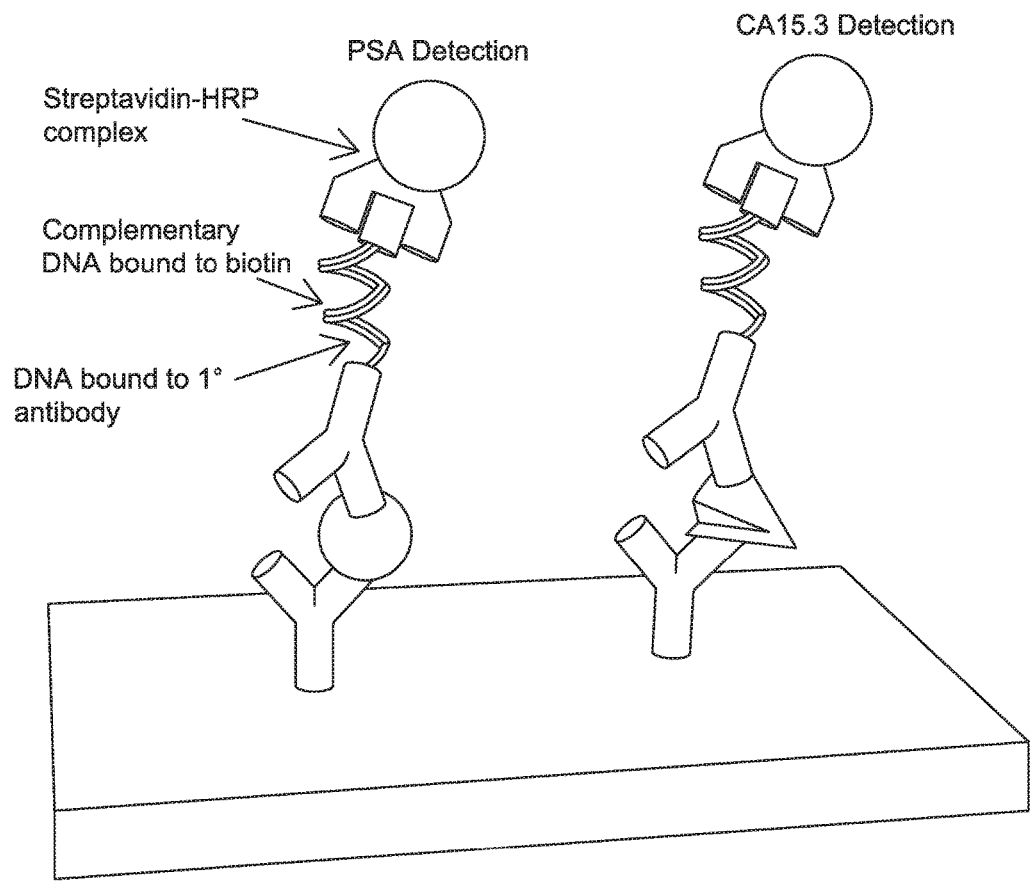

Quantitation of Biomarker of Interest Recovered from the Microfluidic Purification Chip The amount of biomarker recovered from the microfluidic purification chip may be evaluated by a modified ELISA test (FIG. 3C). In a non-limiting procedure, second antibodies to the biomarker of interest are coated on an ELISA plate, using procedures commonly known to those skilled in the art. The coated plates are then washed appropriately to remove excess reagents. The isolated solutions obtained by elution of the microfluidic purification chip after UV irradiation are then added to the coated ELISA plates and equilibrated. After washing, the material in the wells is equilibrated with a probe comprising biotin coupled to the 3'-terminal of a single-stranded DNA oligonucleotide that complements the single-stranded DNA oligonucleotide incorporated in the first antibody conjugate. In one embodiment, the probe is 5'-GCT GCA ACT GAA CCT CTA CGA GTG C-biotin-3' (wherein 5'-GCT GCA ACT GAA CCT CTA CGA GTG C-3' is SEQ ID NO:4). The system is allowed to equilibrate in an appropriate buffer. The system is then treated with streptavidin-horseradish peroxide (HRP), whereby the biotin and streptavidin bind. The system is washed with buffers and treated with a reagent that is used to quantitate HRP, such as 3,3',5,5'-tetramethylbenzidine (TMB). The absorbance of the solution at 450 nm may be evaluated and correlated with amount of biomarker of interest, by using appropriate standards.

Standards are created by exposing antibody-photocleavable biotin conjugates to UV light in solution for 10 min (on ice) and subsequently dialyzing three times with a 100,000 MW cutoff membrane in 1×PBS for 36 hrs total to remove the cleaved biotin, thereby creating antibody-DNA conjugates. These conjugates were used as the detection antibodies in a traditional assay format, where titrated PSA or CA15.3 create the standard.

Fabrication of Nanoribbon Sensor Useful within the Invention

In one embodiment, the nanosensor useful within the invention is a nanoribbon sensor. Such sensors may be produced from silicon-on-insulator wafers with an active and a buried oxide (BOX) layers. Such sensors may also be produced from moldable plastic. In one embodiment, the doping in the active and handle wafers is boron (p-type). The nanosensors may be generated by the method discussed in the Materials section. Optical micrographs of completed devices are shown in the inset in FIGS. 8 and 9A.

The sensor may be derivatized with a second antibody directed to the biomarker of interest. In one embodiment, the second antibody binds to a different biomarker epitope than the first antibody conjugated to the biotinylated-photocleavable crosslinker. After derivatization, the surface of the sensor may then be blocked with a protein such as FBS.

Optimization of detection by the sensor may be achieved by characterizing the drain-source current ($I_{DS}$) versus drain-source voltage ($V_{DS}$) dependence at different gate voltage ($V_G$). Such study is exemplified in FIG. 9. In one embodiment, the region of maximum device sensitivity for the gate voltage is $-2.5\ V \geq V_G \geq -6\ V$. In another embodiment, the gate voltage $V_G$ is about $-5$ V.

General Detection of the Biomarker of Interest

In a non-limiting example, FIG. 1 schematically illustrates the operation of the microfluidic purification chip. The avidin-functionalized chip (FIG. 1A) is treated with antibodies to any number of specific biomarkers conjugated to biotinylated, photocleavable crosslinkers containing a specific DNA sequence.

Figure 1B:
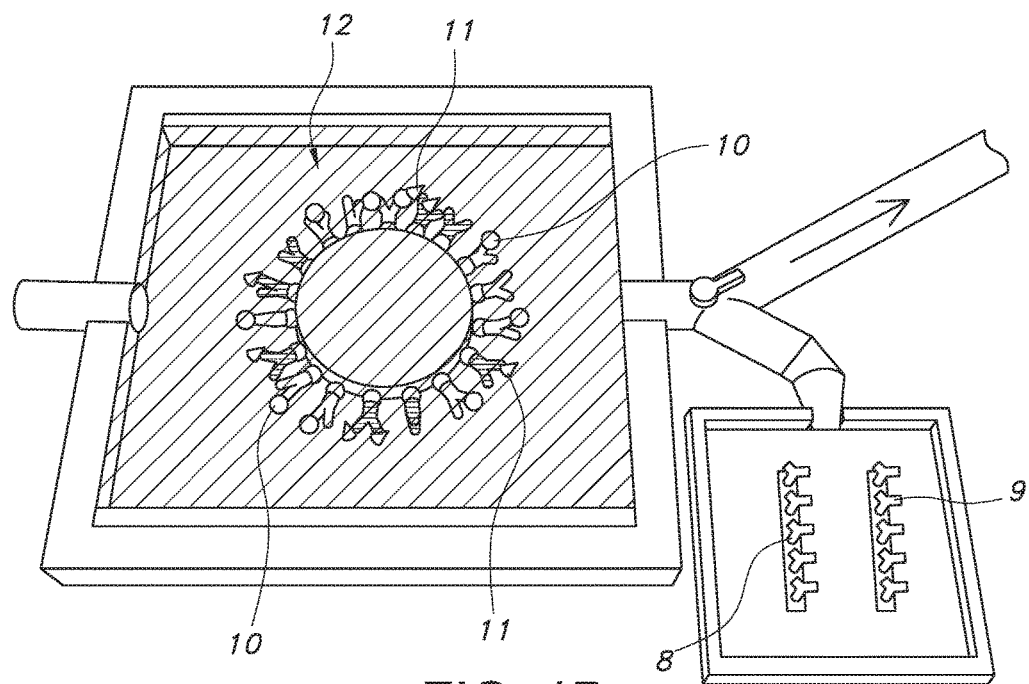
Figure 1C:
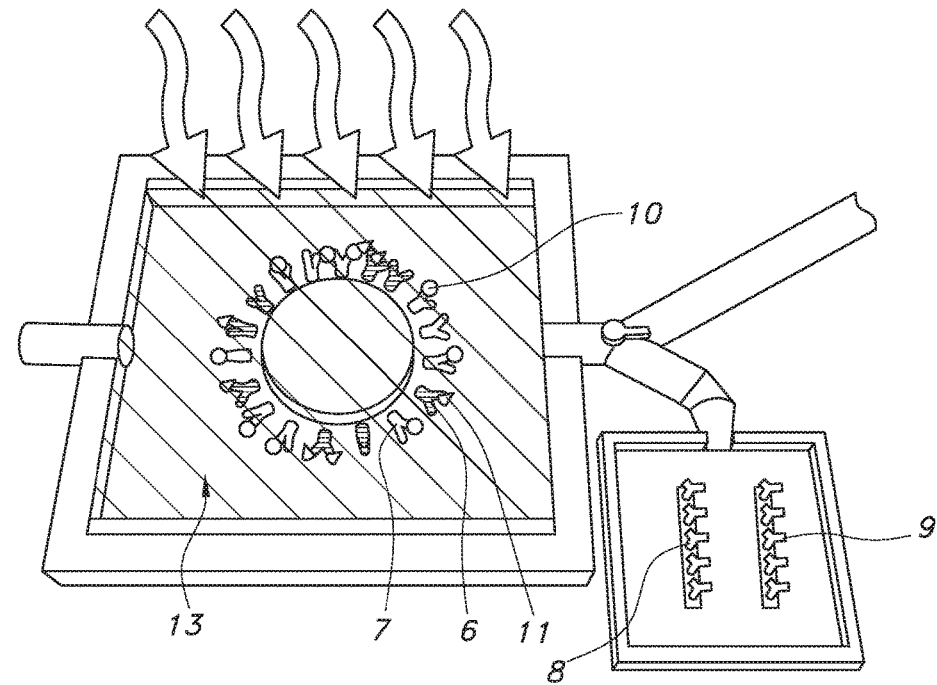
Figure 1D:
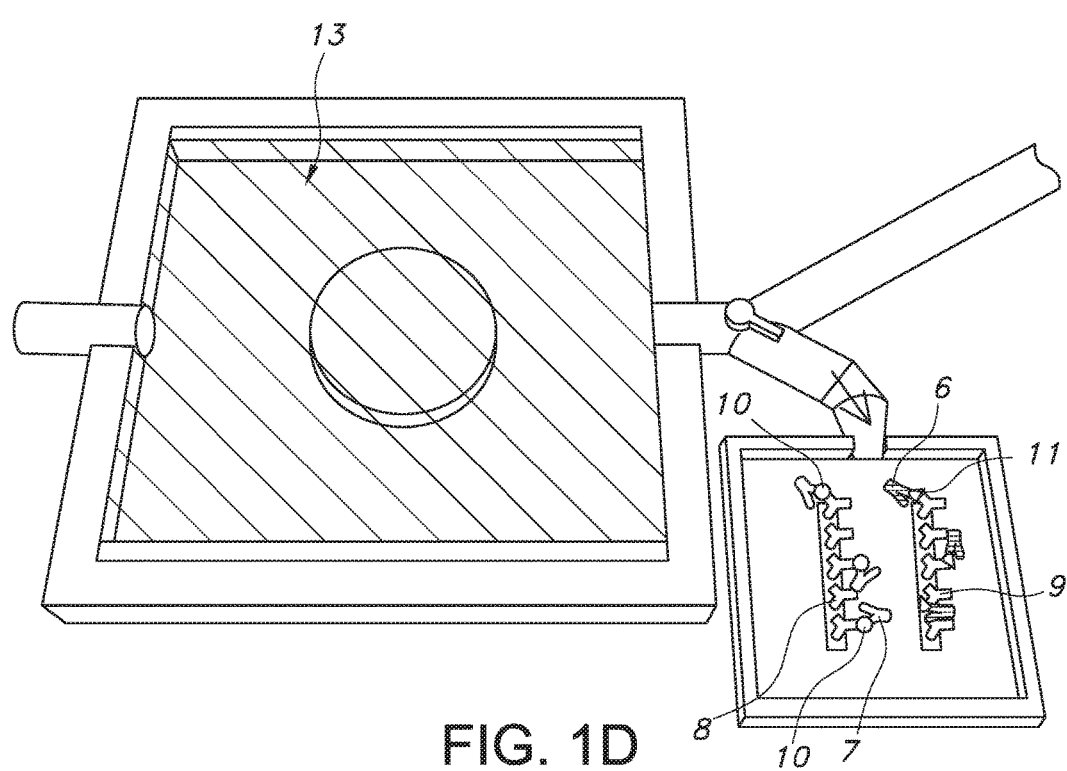

FIGS. 1B, 1C and 1D illustrate the operation of the microfluidic purification chip. A blood sample flows through the chip (FIG. 1B) and the chip-bound antibodies bind specific soluble biomarkers, essentially purifying these molecules from whole blood. After this capture step, wash and sensing buffers are perfused through the device. Flow is then halted, and the sensing buffer-filled microfluidic purification chip is irradiated with ultraviolet (UV) light (FIG. 1C). This results in cleavage of the photolabile group and release of the bound biomarker-antibody-DNA complexes. As shown in FIG. 1D, after a second valve switching step transfers microfluidic purification chip contents to the nanosensor chip, the complexes bind the second antibodies on the nanowire surfaces. The purification/sensing operation thus requires two specific antibody binding events for detection, a significant improvement in selectivity over previous label-free nanosensing schemes.

The methods described herein may be used to estimate the concentration of the biomarker of interest in the physiological solution. A standard quantitative curve may be generated using the methods described herein and employing standard solutions containing known concentrations of the biomarker of interest. Such standard curve may be used to estimate the concentration of the biomarker of interest in the sensing buffer, and this concentration may be used to estimate the concentration of the biomarker of interest in the physiological solution. Any dilutions or concentrations of sample should be taken into consideration in these calculations.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.
Materials and Methods
Modeling Studies Finite element analysis software was used to determine chip parameters to maximize biomarker binding. FIG. 2 shows the modeling results for the final layout. A hexagonal geometry was used because previous studies demonstrated this pattern maximized capture efficiency (Nagrath et al., 2007, Nature 450:1235). Using a flow rate of 10 µL/min during biomarker binding afforded the velocity profile observed in FIG. 2A (streamlines) and FIG. 2B (velocities).

Figure 2A:
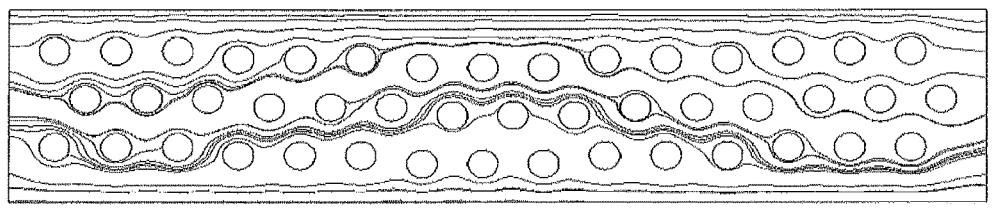
FIGS. 2A-2D, is a series of images illustrating the modeling results for biomarker binding in chips.
Figure 2B:
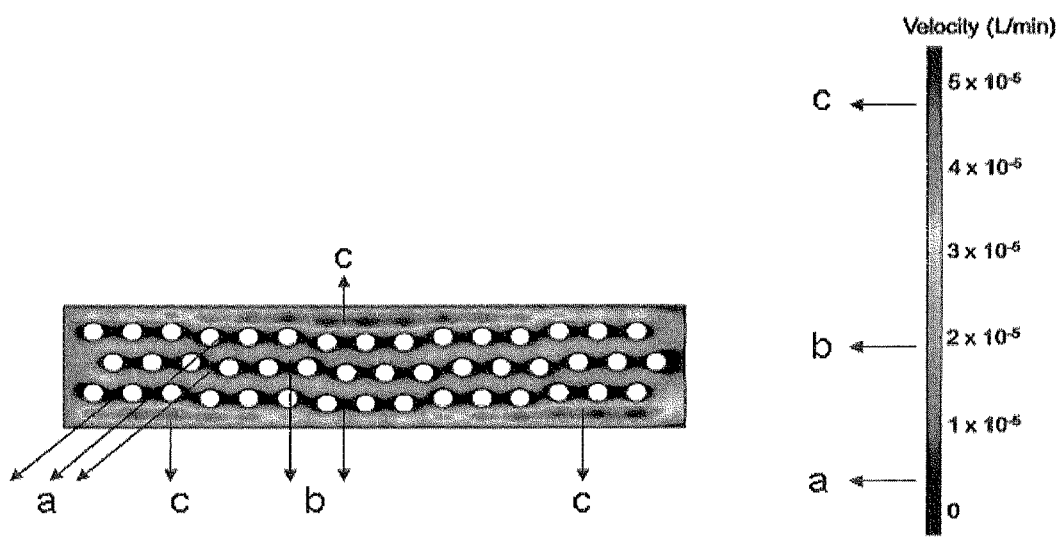
Figure 2C:
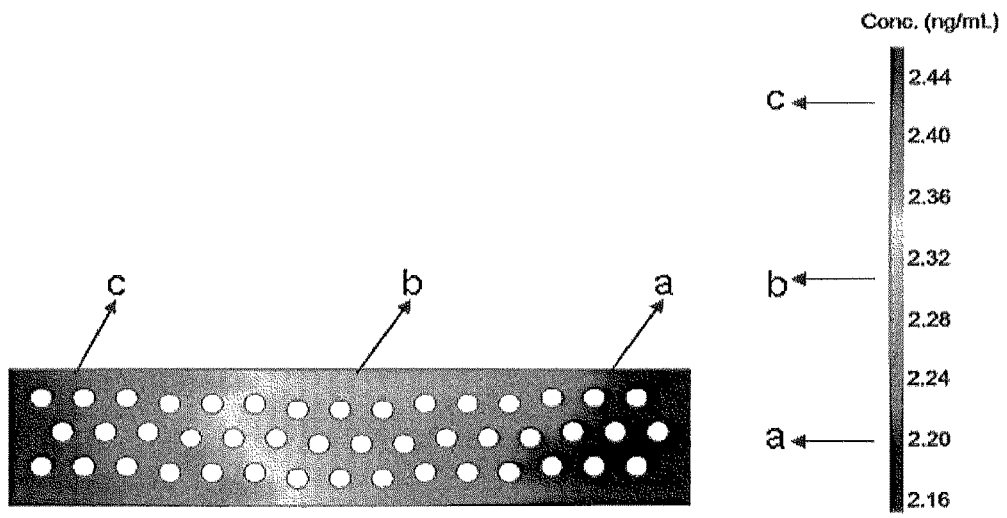
Figure 2D:
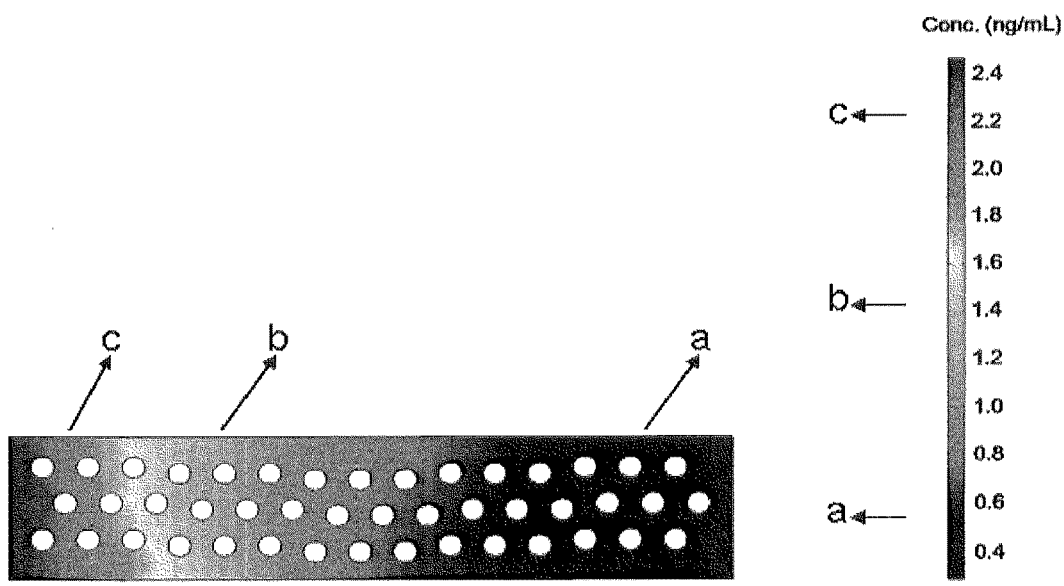

For concentration studies, a prostate specific antigen (PSA) concentration of 2.5 ng/mL was selected because of its clinical relevance (Shariat et al., 2008, Can. J. Urol. 15:4363; Vickers et al., 2009, J. Clin. Oncol. 27:398), with the assumption that nonreversible binding occurred at pillar and wall interfaces. About ~10% of the entering PSA was bound after passing 15 rows of pillars (FIG. 2C). Therefore, 30 rows of pillars were selected for the microfluidic purification chip to enable simultaneous capture of two antigens (FIG. 3B). The chip dimensions were set to width=4 mm, length=7 mm, and height=100 µm, creating a 5 µL volume. Decreasing the flow rate by an order of magnitude increased retention to >80% (FIG. 2D).
Design of Microfluidic Purification Chip Chip dimensions were selected such that the volume of the microfluidic purification chip (5 µL) was equivalent to half the volume in the nanosensing reservoir, thus enabling complete transfer of microfluidic purification chip contents for sensing. The microfluidic purification chip surface area can maximally bind ~500 fmol of biomarker (assuming a 5 nm antibody hydrodynamic antibody radius). Complete release of bound complexes would thus produce a ~100 nM biomarker solution, a value ~$10^6$ greater than that required for any type of sensing. Thus, the chip was suitable for simultaneous purification of multiple biomarkers.
Fabrication of Microfluidic Purification Chip Four inch standard one-side-polished silicon <100> wafers with 200 nm of thermally grown oxide were purchased from Silicon Quest International (Santa Clara, Calif.).

Figure 4:
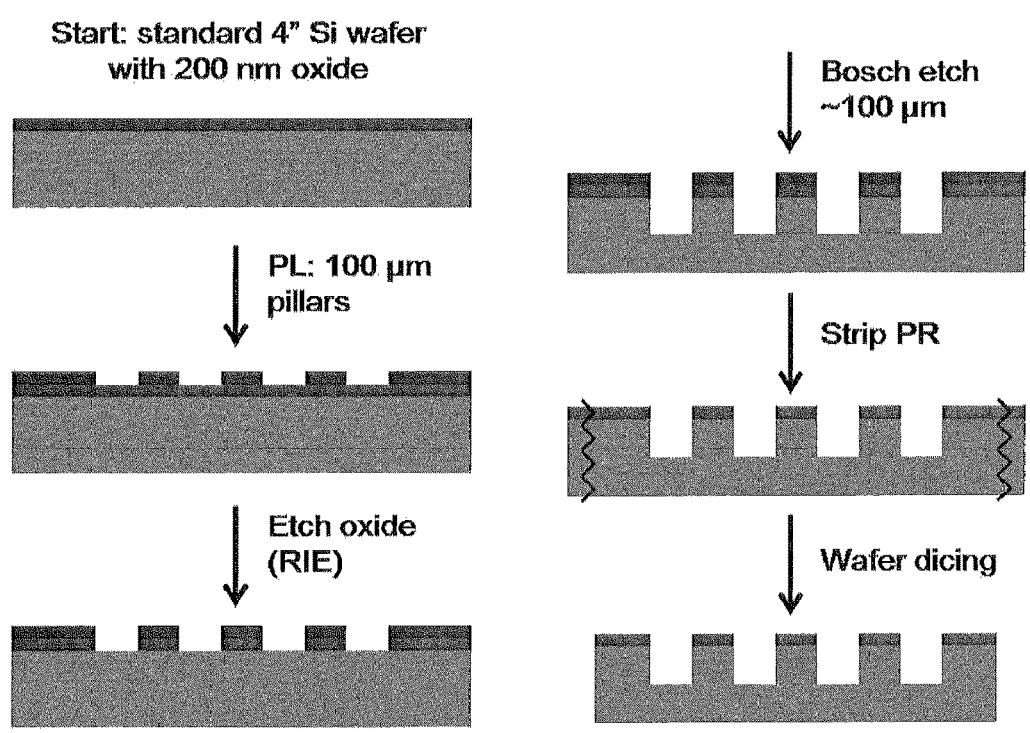
FIG. 4 is a schematic representation of the processing steps performed on standard one-side polished silicon wafers.

All performed processing steps are outlined in FIG. 4. Shipley S1813 photoresist was spun on the wafers and exposed using an EV Group 620 maskaligner and a mask. The pillars were about 100 µm in diameter. Wafers were developed using a Hamatech-Steag automatic wafer processor. The resist pattern was then transferred to the oxide by reactive ion etching (RIB) with an Oxford Instruments PlasmaLab 80 (Oxfordshire, UK). Resist was stripped by ashing in a Branson IPC P2000 barrel etcher (San Jose, Calif.). Silicon pillars about 100 µm deep were realized with a Unaxis 770 Bosch etcher (St. Petersburg, Fla.) and wafers were diced into 4 mm×7 mm chips using a K&S 7100 dicing saw (Fort Washington, Pa.).
Biotinylated-Photocleavable-Antibody Conjugate The photolabile crosslinker was purchased from Yale's W. M. Keck Facility (New Haven, Conn.) and was protected from light at all times. The sequence was 5'-Biotin-photocleavable-CGT AGA GGT TCA GTT GCA GC-amino-3', wherein 5'-CGT AGA GGT TCA GTT GCA GC-3' is SEQ ID NO:3. Antibodies to prostate specific antigen (PSA) were purchased from Accurate Chemical Co. (Westbury, N.Y.) and antibodies to carbohydrate antigen-15.3 (CA15.3) were purchased from Alpha Diagnostics (San Antonio, Tex.). Antibodies were conjugated using 1-ethyl-3-(3-dimethylaminopropyl)carbodiimide (EDC; Pierce Scientific, Rockford, Ill.) & N-hydroxysulfosuccinimide (sulfo-NHS; Pierce Scientific, Rockford, Ill.) chemistry in 1× phosphate buffered saline (PBS) for 1 hour at room temperature with shaking (Hermanson, "Bioconjugate Techniques," Elsevier Science & Technology, New York, 1996).

The conjugates were purified by dialyzing three times with a 100,000 MW cutoff membrane in 1×PBS for 36 hours total and kept frozen at −20° C. Repeated freeze-thaw cycles were avoided and samples were determined to be stable for >14 days at 4° C. The antibody conjugates were protected from light at all times.
Functionalization of the Microfluidic Purification Chip All chemicals were ACS grade or higher and were purchased from Sigma (St. Louis, Mo.) unless otherwise specified. Prior to functionalization, chips were cleaned in a piranha solution (Williams et al., 2003, J MEMS 12:761)—3:1 sulfuric acid (Baker Chemical Company, Phillipsburg, N.J.): hydrogen peroxide (Baker Chemical Company, Phillipsburg, N.J.).

Figure 5:
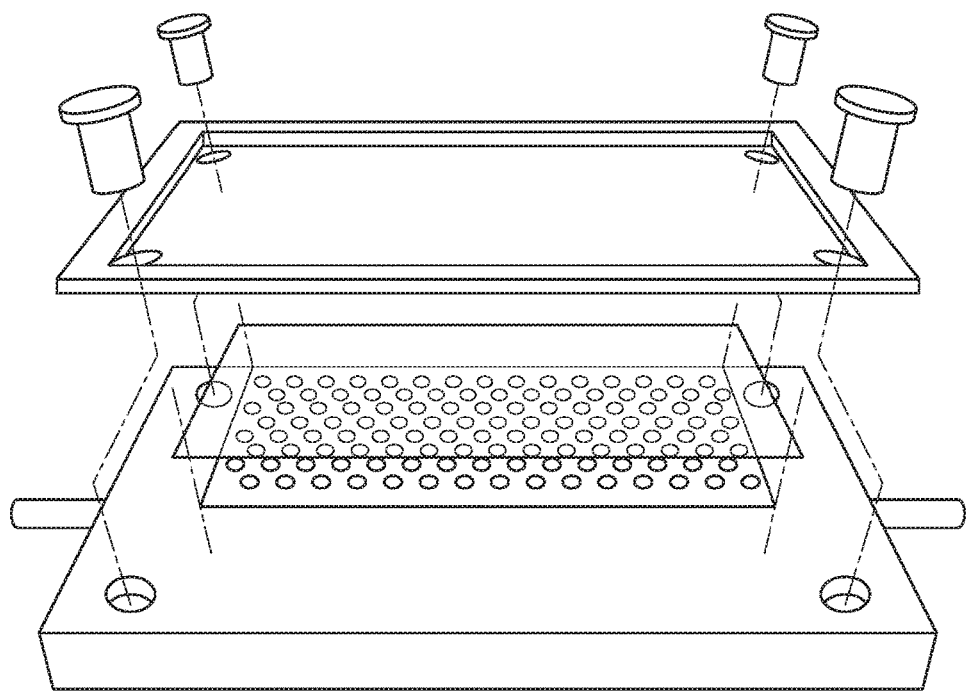
FIG. 5 is a schematic representation of a chip assembly.

Chips were functionalized with 3-aminopropyltriethoxysilane (APTS) according to standard procedures (Emoto et al., 1996, Anal. Chem, 68:3751). Briefly, chips were submerged for 4 hours in a 5% (v/v) solution of APTS in anhydrous toluene in an inert nitrogen atmosphere, rinsed with toluene, and baked in a vacuum oven at 190° C. for 12 hours. Avidin derived from egg white (1 mg/mL; Calbiochem, San Diego, Calif.) was then reacted with the chip surface using EDC/sulfo-NHS chemistry in 1× phosphate buffered saline (PBS) for 1 hour at room temperature with shaking (Hermanson, "Bioconjugate Techniques," Elsevier Science & Technology, New York, 1996). After washing, a 10% (w/v) solution of fetal bovine serum (FBS; Atlanta Biological, Atlanta, Ga.) was introduced to the chips and blocking proceeded for 1 hour at room temperature with shaking. Washing was again performed, after which the biotinylated-photocleavable-antibody conjugates were added to the chip in 1×PBS and reacted for 1 hour at room temperature with shaking. Chips were washed with 1×PBS and loaded into the machined chip assembly (FIG. 3B, inset and FIG. 5). The microfluidic purification chip volume was kept filled with 1×PBS until blood was introduced.
Operation of the Microfluidic Purification Chip For each experiment, 10 µL of whole, heparinized mouse or rate blood was flowed through the chip over the course of 1 min (10 µL/min flow rate). Flow rates were kept constant using a Harvard Apparatus PHD 2000 syringe pump (Holliston, Mass.). Initial washing was performed with 1×PBS at a 25 µL/min flow rate for 3 min. Secondary washing was performed with the sensing buffer, 1 mM bicarbonate buffer, pH 9.0 at a 25 L/min flow rate for 1 min. The valve was then closed and a UV light source, a Blak-Ray Long-Wave UV lamp (Upland, Calif.), at a 10 cm distance, was used to irradiate the chip for 10 min. The chip/holder was kept on ice for the duration of UV irradiation to regulate the temperature.

Experiments with Chicken Egg Ovalbumen (OVA)

Anti-OVA antibodies were purchased from Immunology Consultants Laboratories (Newberg, Oreg.) and conjugated to the biotinylated photocleavable linker and bound to the microfluidic purification chip as described above.

Whole heparinized blood was obtained from a C56Bl/6 mouse and stored at 4° C. until use. The sample was spiked with OVA-conjugated fluorescein-5-isothiocyanate (FITC) obtained from Invitrogen (Carlsbad, Calif.) at a concentration of 10 µg/mL. Imaging was performed with a Zeiss fluorescence microscope (Thornwood, N.Y.). The same exposure time was used for all image captures.

Post-UV Retained Immunoactivity Studies

Figure 6:
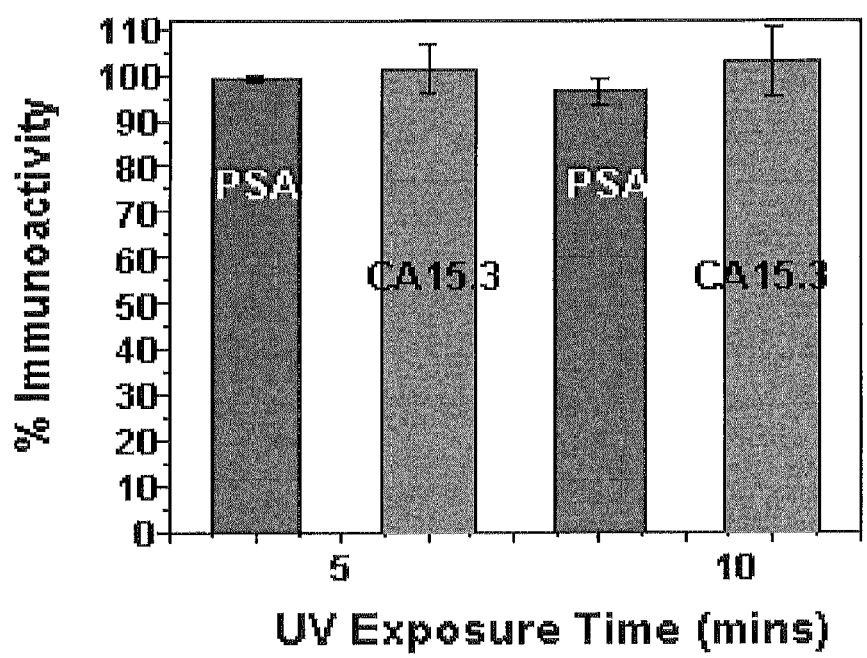
FIG. 6 is a bar graph summarizing the immunoactivity determination of PSA and CA 15.3 by ELISA assays after UV irradiation.

Nearly 100% of PSA and CA15.3 immunoreactivity was retained after UV irradiation (FIG. 6), demonstrating that the cleavage step did not compromise subsequent binding of complexes to nanosensor-bound second antibodies. Prostate specific antigen (Accurate Chemical Co., Westbury, N.Y.) and CA15.3 (Alpha Diagnostics, San Antonio, Tex.) were diluted to 2.5 ng/mL and 30 U/mL concentrations, respectively, in 1×PBS and irradiated with UV light in for 5 or 10 min. Enzyme-linked immunoassays (ELISAs) obtained from Accurate Chemical Co. (Westbury, N.Y.) and Alpha Diagnostics (San Antonio, Tex.) were used for immunoactivity determination of PSA and CA15.3, respectively. Percent immunoactivities were obtained by dividing pre- and post-UV irradiation concentration values determined by ELISA for each antigen. Each bar represents the average of three experiments and error bars represent one standard deviation. In order to minimize sample heating, chips were placed on ice for the duration of irradiation.

Modified ELISA Assay

Second antibodies were coated on 96-well ELISA plates (BD Scientific, Research Triangle Park, N.C.) in coating buffer (0.1 M bicarbonate buffer, pH 9.0) overnight at 4° C. A 10% FBS solution was added and blocking was performed for 1 hour at room temperature. A platewasher (Labsystems Wellwash 4 Mk2, Basingstoke, UK) was used to wash the plates with 0.05% Tween 20 in 1×PBS (Sigma, St. Louis, Mo.) for this and subsequent washing steps. Microfluidic purification chip-purified samples (5 µL) were added to the wells in addition to 5 µL of 1×PBS and binding proceeded for 2 hours at room temperature. After washing, DNA hybridization was performed for 2 hours at room temperature in 1×SSC buffer (Promega, Madison, Wis.) with 0.05% sodium dodecyl suflate (SDS) and 0.1% bovine serum albumin, as described previously for solid-phase binding (Bailey et al., 2007, J. Ame. Chem. Soc. 129:1959). Washes were performed manually with 1×SSC with 0.05% SDS. The biotinylated sequence was 5'-GCT GCA ACT GAA CCT CTA CGA GTG C-biotin-3' and was purchased from W. M. Keck Facility (New Haven, Conn.). Washing was again performed, followed by the addition of the streptavidin-HRP conjugate (BD Biosciences, Research Triangle Park, N.C.)) at 10 µg/mL in 1× PBS, Then, 3,3',5,5'-tetramethylbenzidine (TMB) was added to the wells and the reaction proceeded for 5-10 minutes at room temperature in the dark until visual inspection dictated that it be stopped with 0.1 M sulfuric acid (Baker Chemical Co., Phillipsburg, N.J.). Absorbances were then read at 450 nm with a Molecular Devices SpectraMax M5 plate reader (Sunnyvale, Calif.).

Standards were created by exposing antibody-photocleavable biotin conjugates to UV light in solution for 10 min (on ice) and subsequently dialyzing three times with a 100,000 MW cutoff membrane in 1×PBS for 36 hours total to remove the cleaved biotin, thereby creating antibody-DNA conjugates. These conjugates were used as the detection antibodies in a traditional assay format, where titrated PSA or CA 15.3 created the standard.

Fabrication of Nanoribbon Sensor

Figure 7:
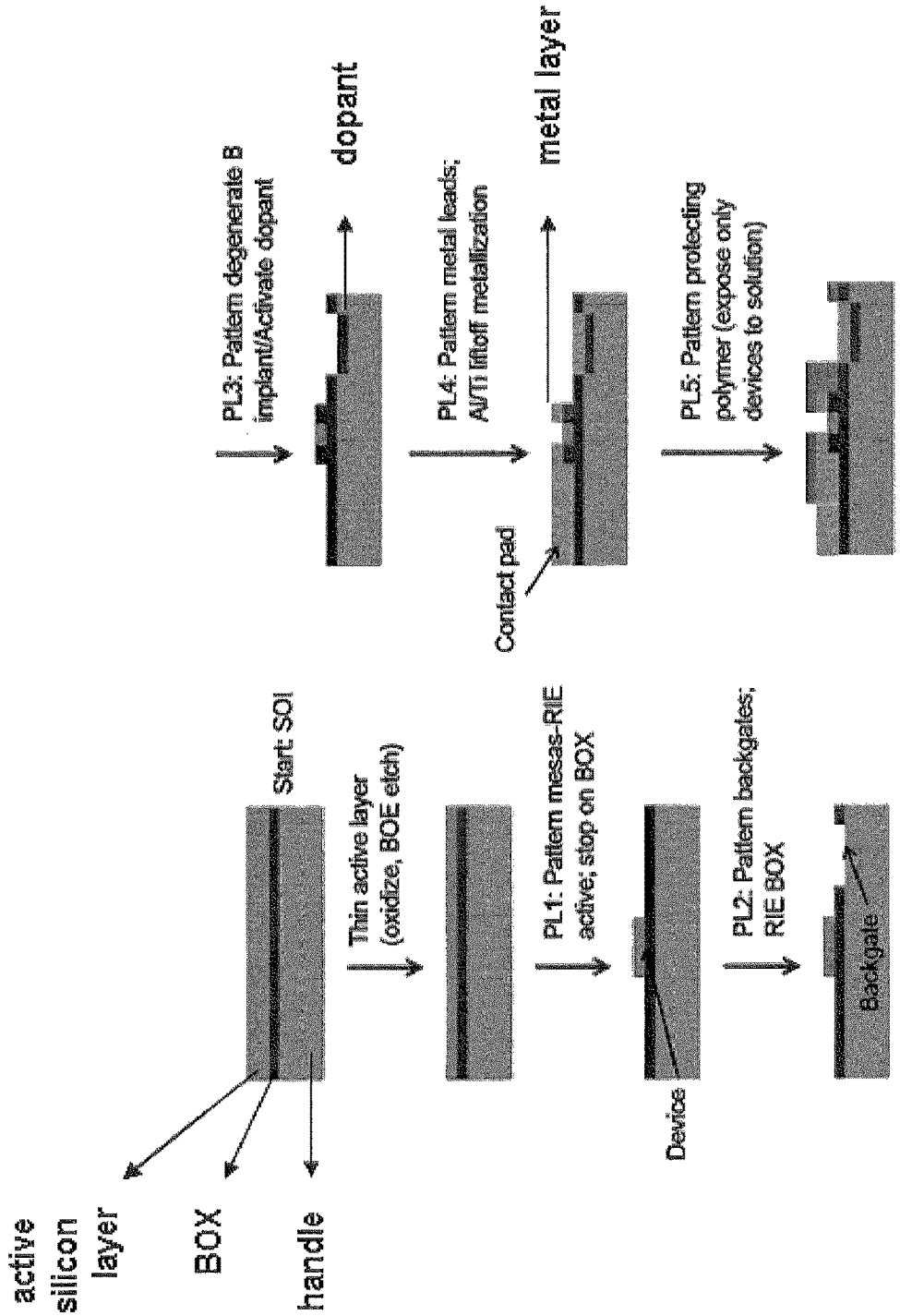
FIG. 7 is a schematic representation of the fabrication of a nanoribbon sensor.

Eight inch silicon-on-insulator wafers with a 70 nm active and 145 nm buried oxide (BOX) layer were purchased from SOITEC (Bernin, France) and are illustrated in FIG. 7. The doping in the active and handle wafers was boron (p-type) at $10^{15}$ cm$^{-3}$. The wafers were laser-cut to 4-inch diameters by Silicon Quest International (Santa Clara, Calif.). All photolithography steps were performed using Shipley S1808, S 1813, or S 1827 photoresist (Rohm & Haas, Philadelphia, Pa.) and an EV Group 620 maskaligner. All masks were 5" and were purchased from PhotoSciences, Inc. (Torrance, Calif.). The active layer was thinned to 25 nm by thermal growth of a ~98 nm oxide at 1000° C. using a MRL Industries furnace after MOS cleaning (Muller and Kamins, In "Device Electronics for integrated circuits", 2nd Ed., John Wiley & Sons, NY, N.Y., 1986). Oxide thickness was determined using a Woollam Variable Angle Spectroscopic Ellipsometer (Lincoln, Neb.).

The silicon mesas were patterned in the first photolithographic (PL) step and chlorine reactive-ion etching (RIE) was performed using an Oxford PlasmaLab 100 RIE. This chemistry did not etch oxide, thus the BOX served as an etch-stop. Photoresist was stripped by ashing using a Mercator Control System Inc. HF-6 barrel asher.

The second PL step patterned contacted to the silicon handle wafer to serve as electronic backgates for device characterization. Vias through the BOX to the backgate were etched using 10:1 buffered oxide etch (BrandNu Labs, Meriden, Conn.) and photoresist was stripped using acetone and isopropanol (BrandNu Labs, Meriden, Conn.).

The third PL step patterned degenerate doping regions for contacts to device and backgate contacts. A boron implant dose of $5\times10^{15}$ cm$^{-2}$ at 8 KeV was performed at a 7° tilt by Core Systems. Photoresist was stripped by ashing, followed by wafer exposure to piranha solution. The dopant was activated by annealing the wafers at 900° C. in nitrogen in a MRL Industries furnace after MOS cleaning.

The fourth PL step patterned metal leads, pads, and contacts. A 75 nm Al (99.99%, Kurt J. Lesker Co.)/75 nm Ti (99.9%, Kurt J. Lesker Co.) liftoff evaporation was performed by electron-beam deposition in a Kurt J. Lesker EJ1800 Thin Film Deposition System. After liftoff, achieved by wafer sonication in acetone, the wafers were rapid-thermal annealed (RTA) for 1 min at 650° C. in a Surface Sciences Integration Solaris 150 RTA. Sequential RTA/electrical characterization steps (see below) dictated that these conditions were required in order to form Ohmic contacts to devices (Muller and Kamins, In "Device Electronics for integrated circuits", 2nd Ed., John Wiley & Sons, NY, N.Y., 1986).

The fifth PL step patterned S 1808 photoresist as a passivating layer across the chip to prevent leakage. Exposed surfaces included contacts and active device regions (black arrow, FIG. 8D). The photoresist was hard-baked for 1 hour at 140° C. This step was performed after APTS functionalization as resist was dissolved by the organic solvents required for that process. Optical micrographs of completed devices are shown in the inset in FIGS. 8 and 9A. In FIG. 8, consecutive zooms are shown corresponding to dashed boxes.

Functionalization of the Sensor

The passivation layer was deposited by PL after APTS functionalization. Devices were diced with a glass scribe and functionalized with either anti-PSA (Accurate Chemical Co.) or anti-CA15.3 (Alpha Diagnostics) using standard EDC/sulfo-NHS chemistry in 1×PBS, pH 7.4. These antibodies bound different epitopes of PSA and CA15.3, respectively, to those conjugated to the biotinylated-photocleavable crosslinker. After washing with 1×PBS, the surface was blocked with a 10% FBS solution and subsequently washed with 0.01×PBS. Reservoirs were filled with 5 µL of 0.01× PBS and remained filled with this volume until sensing measurements were performed.

Electrical Characterization Measurements

Figure 9A:
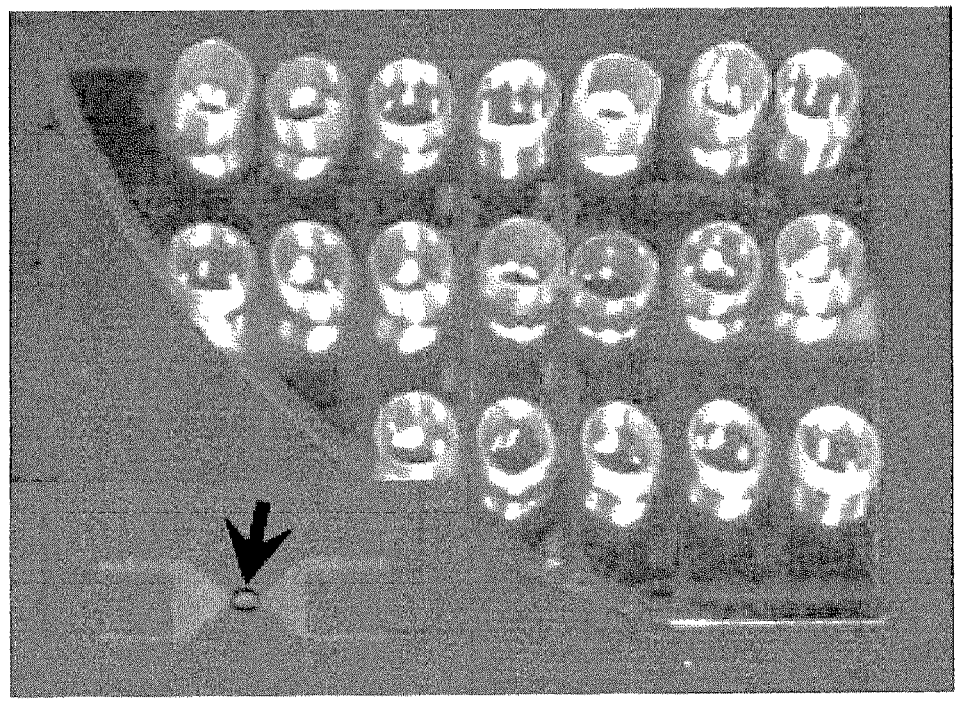
FIGS. 9A-9D, is a series of images illustrating electrical characteristics of nanosensors.
Figure 9B:
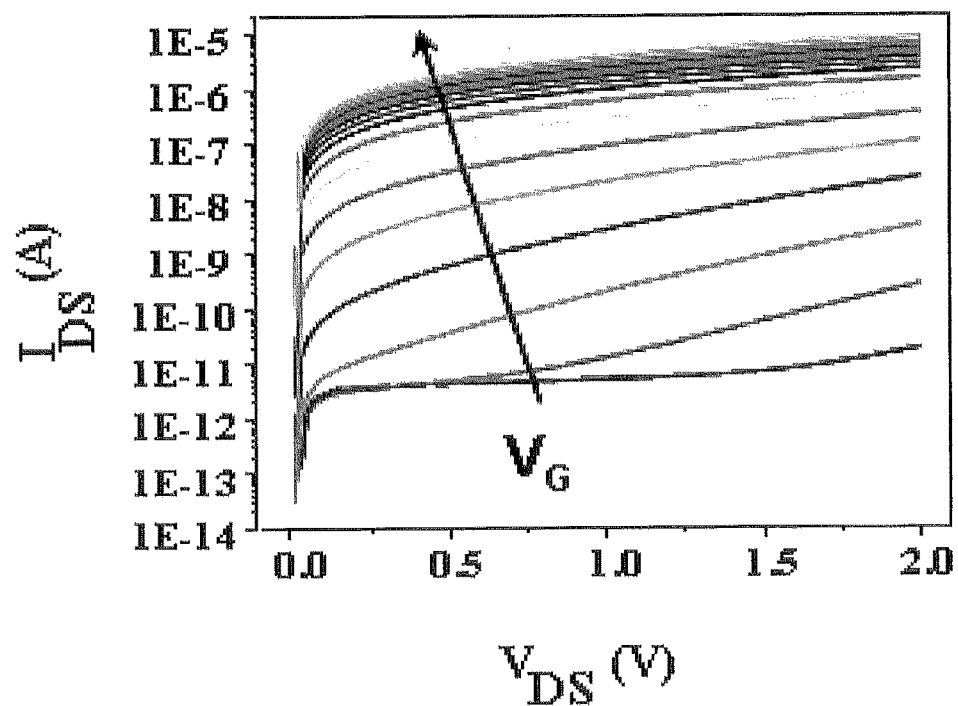
Figure 9C:
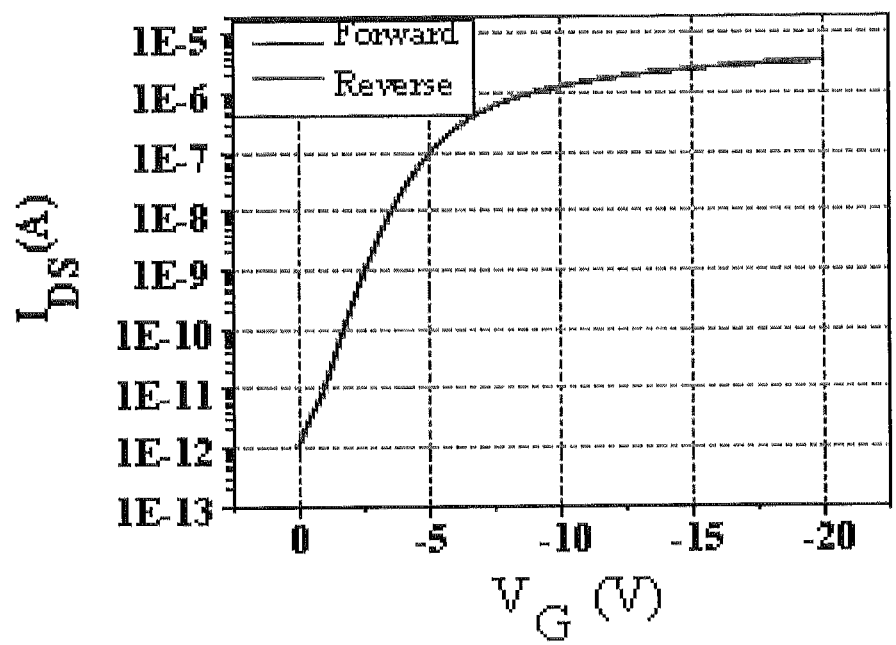
Figure 9C:
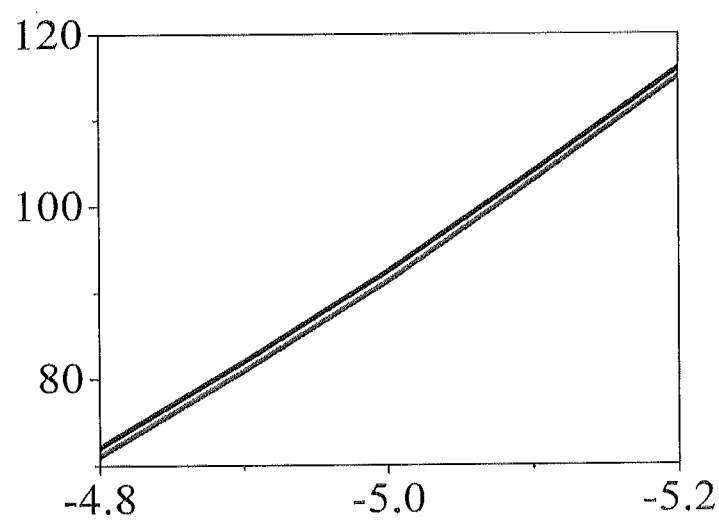
Figure 9D:
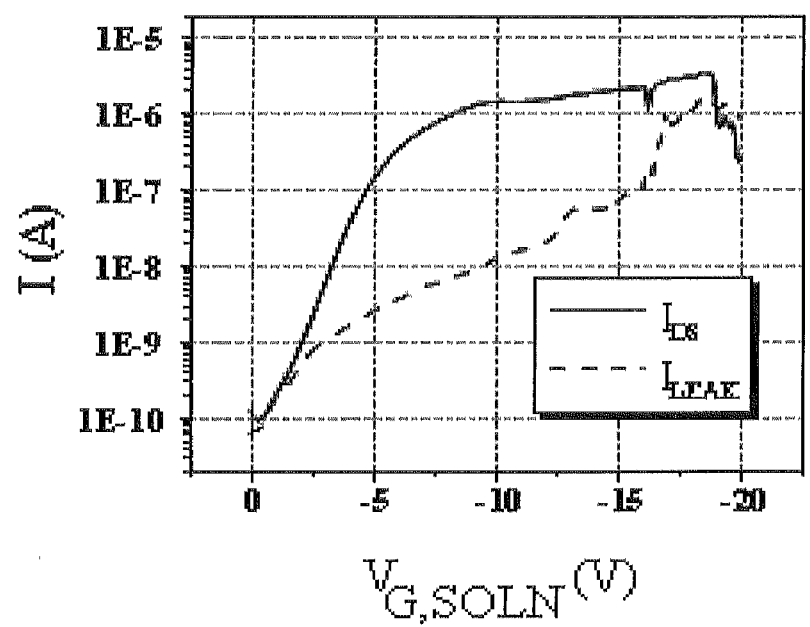
Figure 10A:
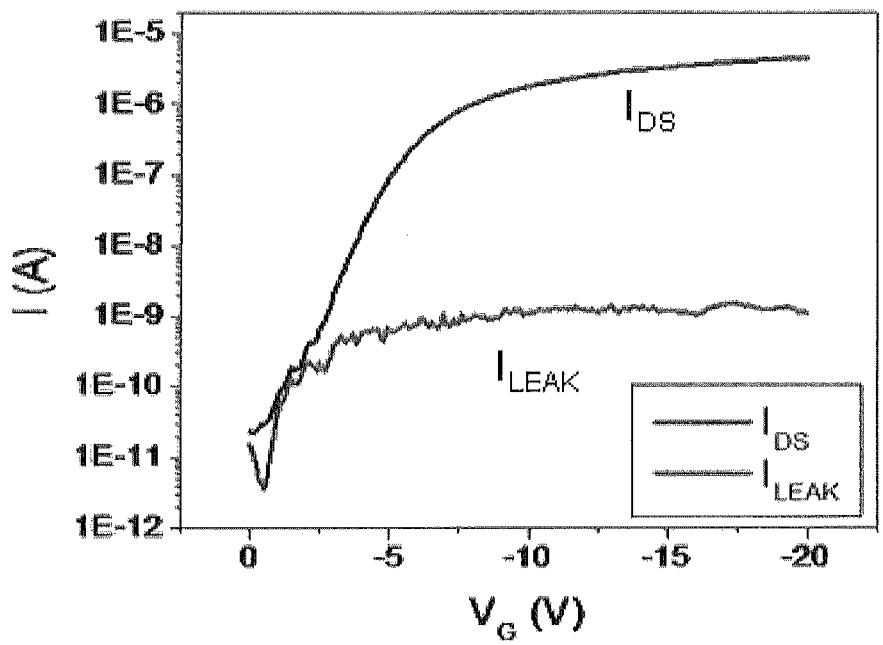
FIGS. 10A-10C, is a series of graphs illustrating the correlation of I with $V_G$.
Figure 10B:
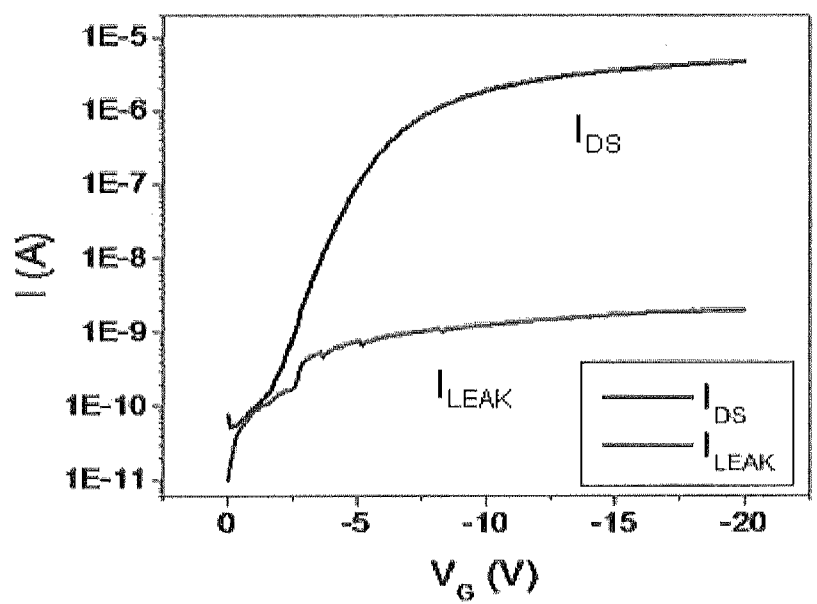
Figure 10C:
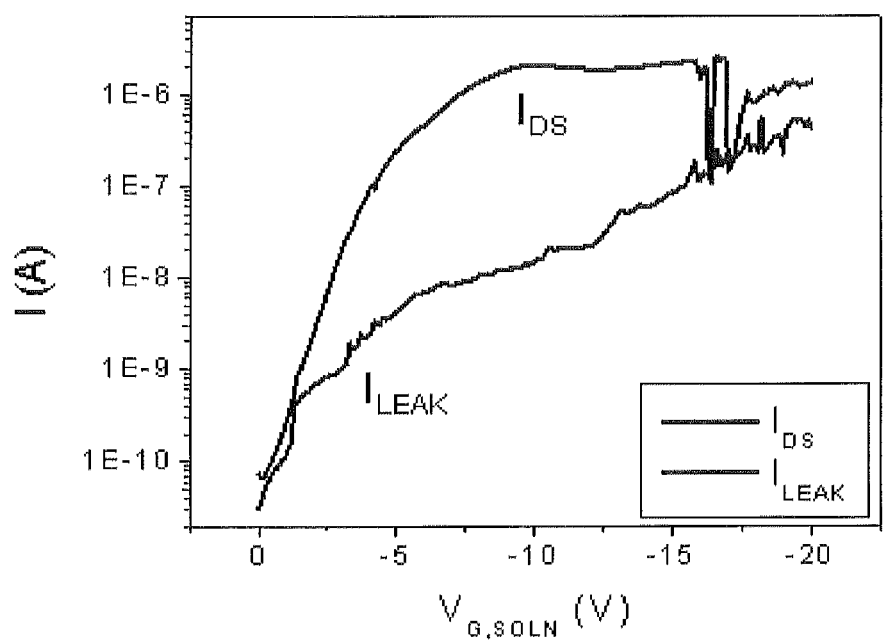
Figure 11A:
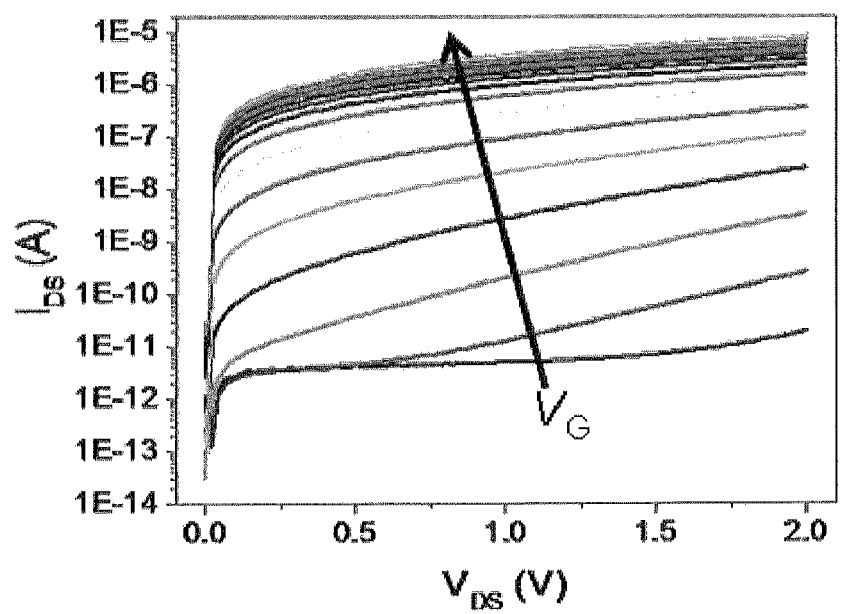
FIGS. 11A-11D, is a series of graphs illustrating the correlation of $I_{DS}$ with V.
Figure 11B:
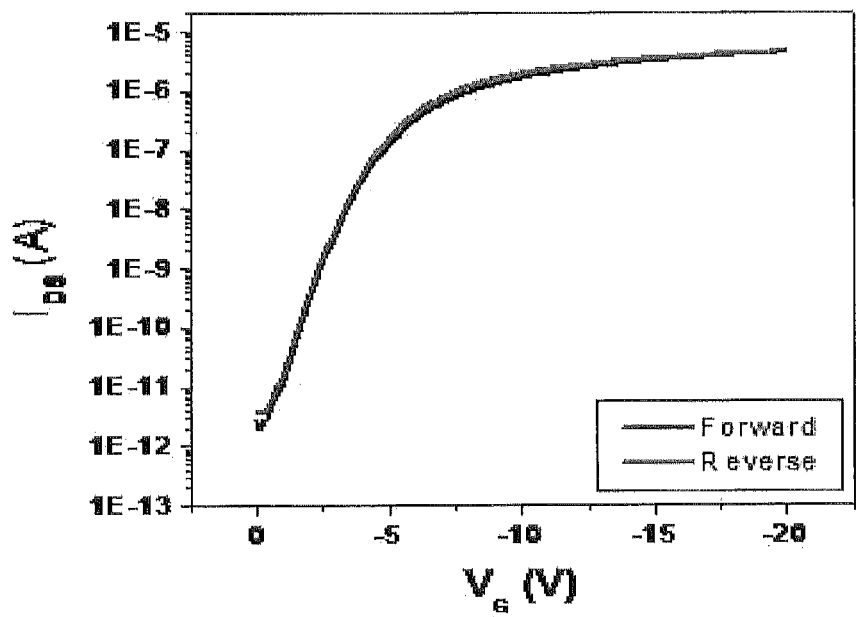
Figure 11C:
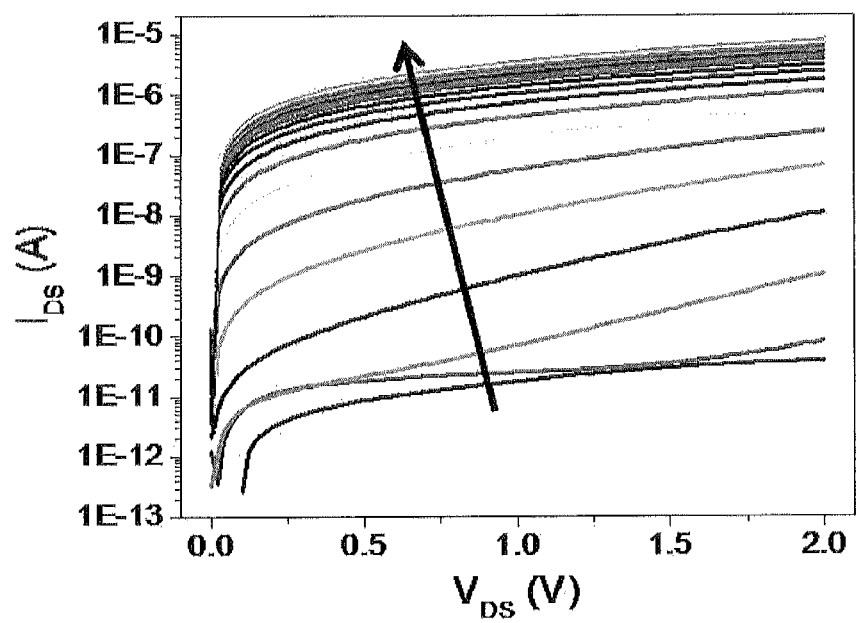
Figure 11D:
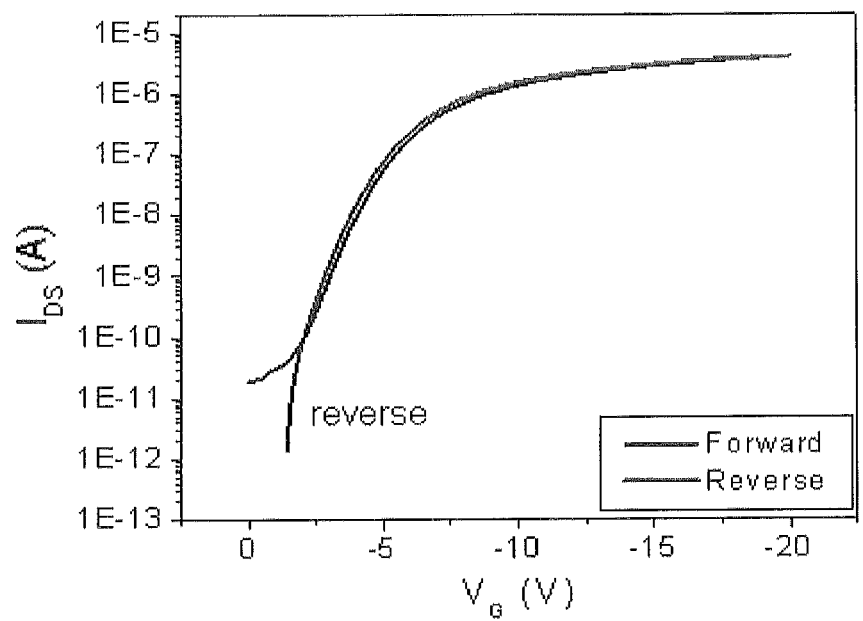

Devices were characterized with an Agilent Systems 4156C Semiconductor Parameter Analyzer (SPA). A single, representative device is illustrated in FIGS. 9 and 10. Characterization prior to functionalization is illustrated in FIGS. 9B-C. The drain-source current ($I_{DS}$) versus drain-source voltage ($V_{DS}$) dependence for increasing negative gate voltage ($V_G$) in −1V steps is illustrated in FIG. 9B. In all $I_{DS}(V_G)$ plots the black arrow indicates the direction of increasing negative $V_G$. The $I_{DS}(V_G)$ plot at $V_{DS}$=−1V shows negligible hysteresis for forward and reverse sweeps (FIG. 9C). Post-APTS functionalization, the $I_{DS}(V_{DS})$ and $I_{DS}(V_G)$ dependencies are illustrated in given in FIGS. 11A and 11B, respectively. The hysteresis was minimally increased. After complete functionalization and FBS blocking, the $I_{DS}(V_{DS})$ dependence is illustrated in FIG. 11C and the $I_{DS}(V_G)$ dependence in FIG. 11D. The hysteresis was minimally increased, although low-$V_G$ potentials (0 to −2.5V) may suffer from significant charging effects. Solution gating using an exposed electrode in the sensing reservoir (FIG. 8C) to sweep the potential of the ionic solution ($V_{G,SOLN}$) demonstrated that device current ($I_{DS}$) levels were >100-fold larger than device-to-solution leakage current in the operating window for the device (−4 V≥$V_G$≥−15 V) and that the region of maximum device sensitivity was −2.5 V≥$V_G$≥−6 V (FIG. 9D).

Solution-Phase Sensing

Figure 8A:
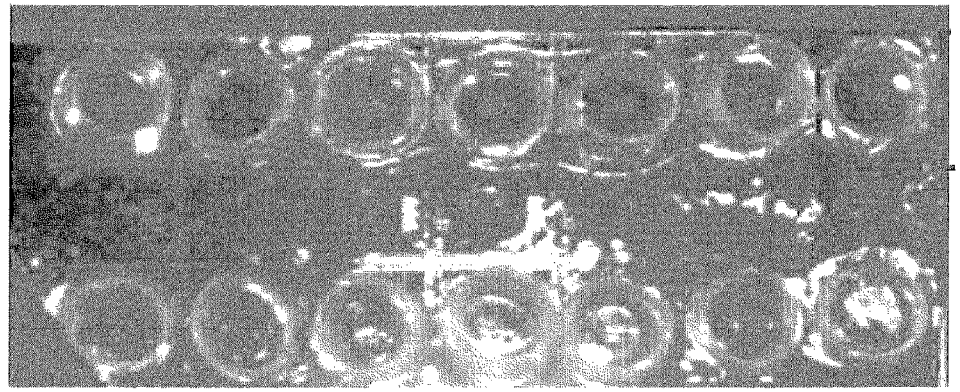
FIGS. 8A-8D, is a series of images representing optical micrographs of nanoribbon sensors.
Figure 8B:
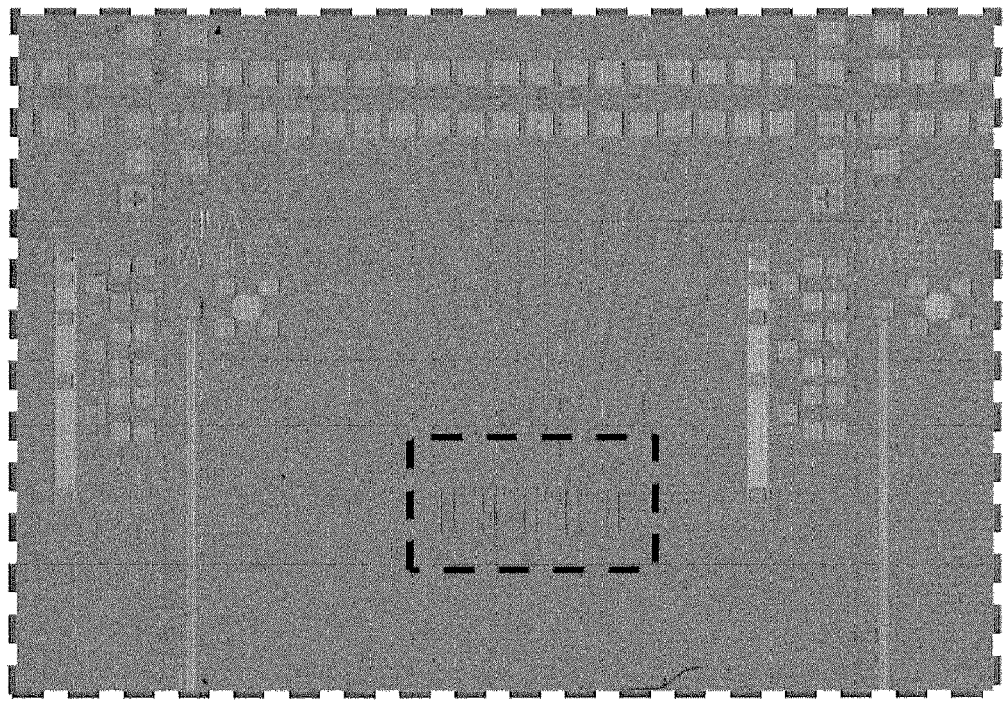
Figure 8C:
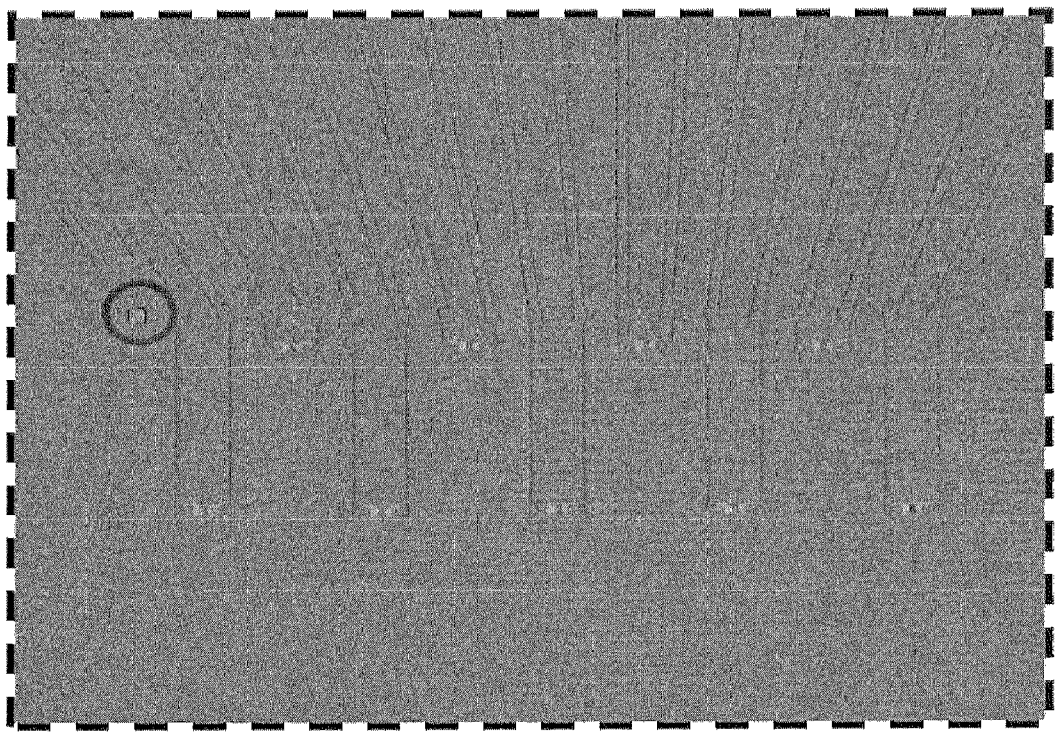
Figure 8D:
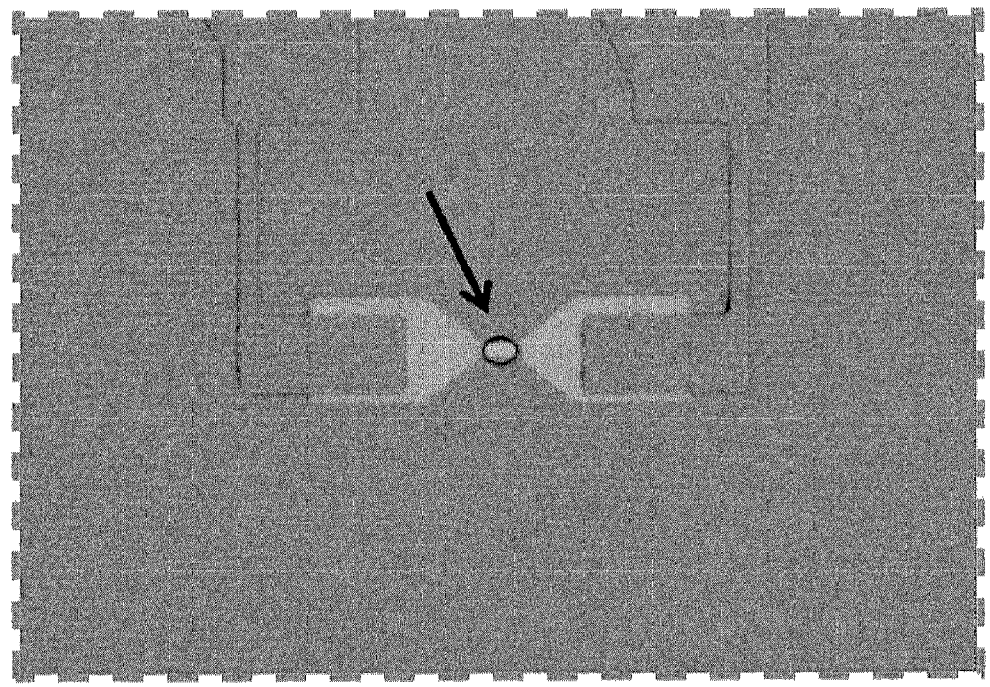

Reservoirs were created by epoxying thin-walled, PTFE tubing to the chip (Stern et al., 2007, Nature 445:519). Solution-gating was performed using an exposed electrode on the chip surface (circle, FIG. 8C). Representative devices functionalized with anti-PSA or anti-CA15.3 antibodies were gated in the presence of 10 µL of sensing buffer in the reservoir. Anti-PSA and anti-CA15.3-functionalized device backgating (using the handle wafer) is illustrated in FIGS. 10A and 10B, respectively, and solution gating is illustrated in FIG. 9D and FIG. 10C, respectively. All devices used in this experiments were 1 µm in width and had a 2 µm length exposed to the sensing solution (FIG. 8D). For the solution phase sensing measurements, a 1 mM bicarbonate buffer solution was used, which has a Debye screening length of $\lambda_D$=9.6 nm. To verify that the signal from binding proteins would not be screened by the buffer solution, direct measurements of the amount of the signal that would be unscreened were carried out by varying buffer salt concentration (Stern et al., 2007, Nano Lett. 7:3405). After protein injection and stabilization in the 1 mM bicarbonate buffer ($\lambda_D$=9.6 nm), the solution was then changed to a low ion concentration buffer (0.1 mM bicarbonate), which should extend the Debye length to ~30 nm. The signal was observed to increase, to its maximum unscreened value. A high salt concentration was then added (10 mM NaCl, $\lambda_D$~3 nm), and the signal was observed to decrease far below the initial (absorbed protein) value, and close to baseline. Nine devices for CA15.3 gave an average of 61% unscreened (1.6% SEM—standard error of the mean, 1 mM bicarbonate buffer). Twenty PSA devices gave a slightly lower value of unscreened (46%, 2.6% SEM, 1 mM bicarbonate buffer).

Sensing Measurements

Figure 12A:
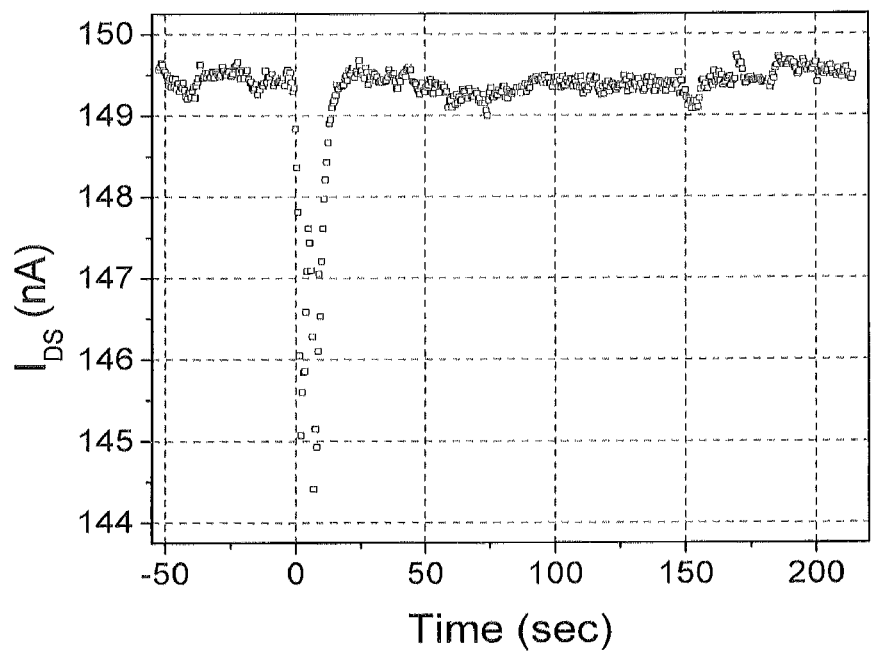
FIGS. 12A-12B, is a series of graphs illustrating the response of an anti-PSA functionalizing device to CA15.3 (FIG. 12A) and of an anti-CA15.3 functionalized device to PSA (FIG. 12B) in sensing buffer.
Figure 12B:
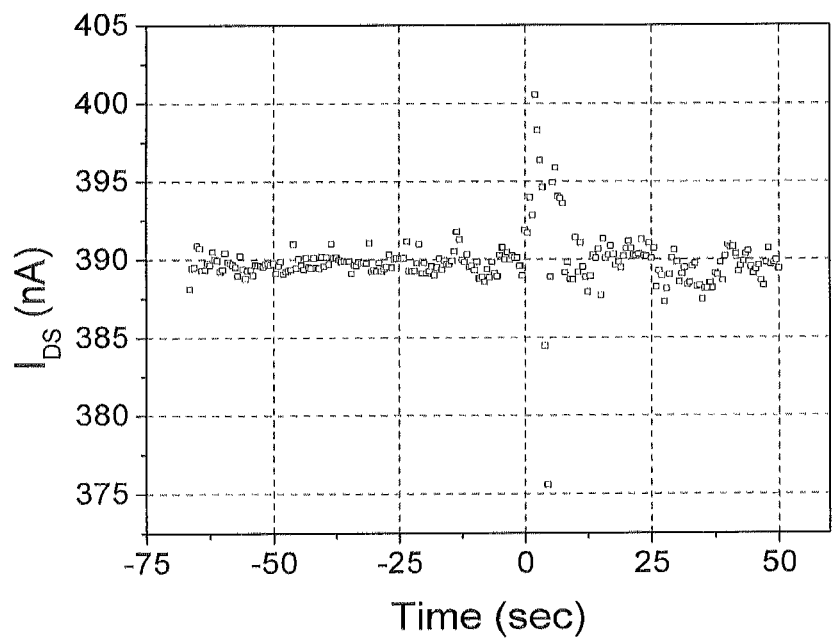

For all sensing measurements the SPA was used in sampling mode, measuring $I_{DS}$ at 0.5 sec intervals, and mixing was performed with manual pipetting. As observed previously, injection transient noise was present in all measurements (Stern et al., 2007, Nature 445:519) and devices required 1-5 mins for current stabilization in sensing buffer (Stern et al., 2007, Nano Lett. 7:3405). The sensing reservoir was filled with 5 µL of pure sensing buffer and, after device current stabilization, the solution to be sensed was added. For consistency, solution addition is defined as occurring at time=0. The response of an anti-PSA functionalized device to a 2.25 U/mL concentration of CA15.3 in sensing buffer is illustrated in FIG. 12A, and the response of an anti-CA15.3 functionalized device to a 0.4 ng/mL concentration of PSA in sensing buffer is illustrated in FIG. 12B. The absolute device responses (not normalized) of anti-PSA and anti-CA 15.3 functionalized devices to the spiked buffer sample (FIG. 14A and FIG. 14B) are given in FIGS. 11A and 11B, respectively. For all pure buffer sensing measurements, 5 µL of the sample was added to the reservoir.

Figure 13A:
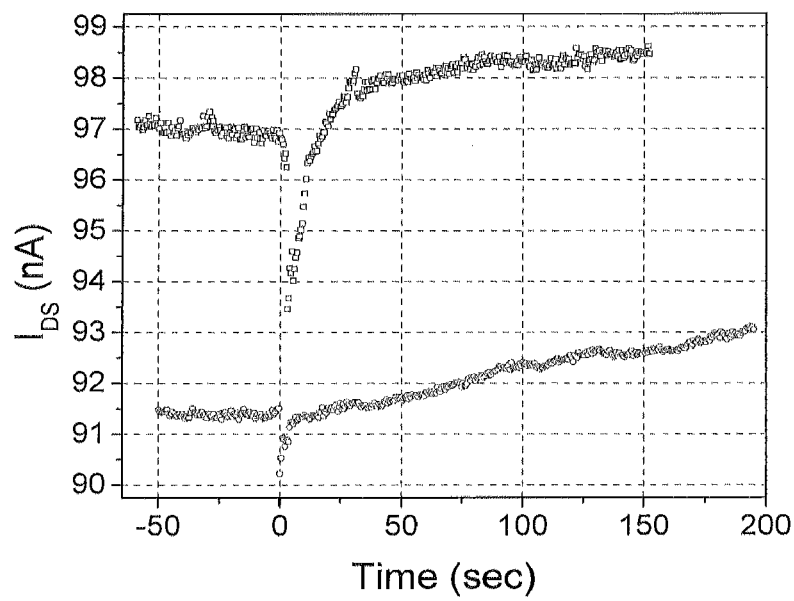
FIGS. 13A-13F, is a series of graphs illustrating absolute sensor responses.
Figure 13B:
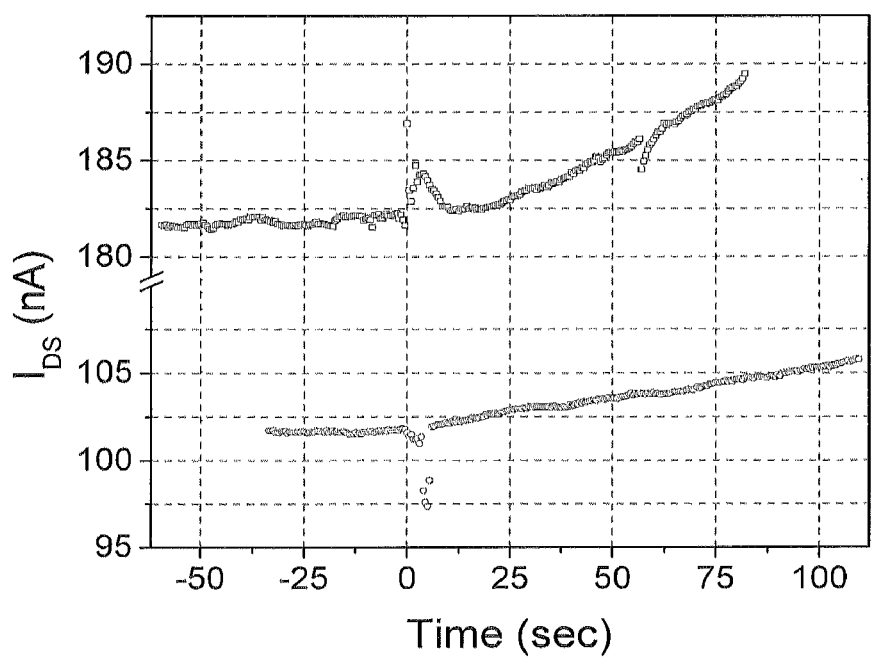
Figure 13C:
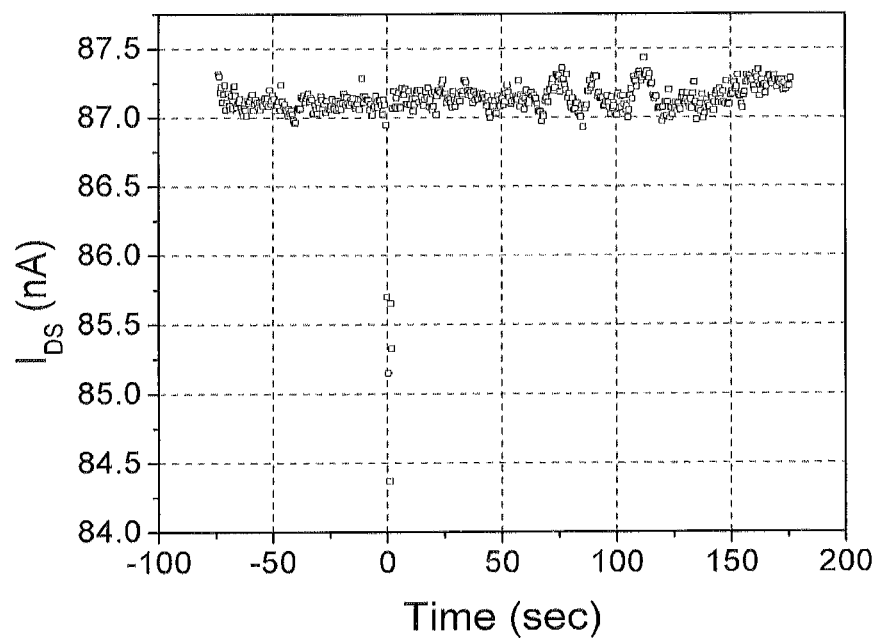
Figure 13D:
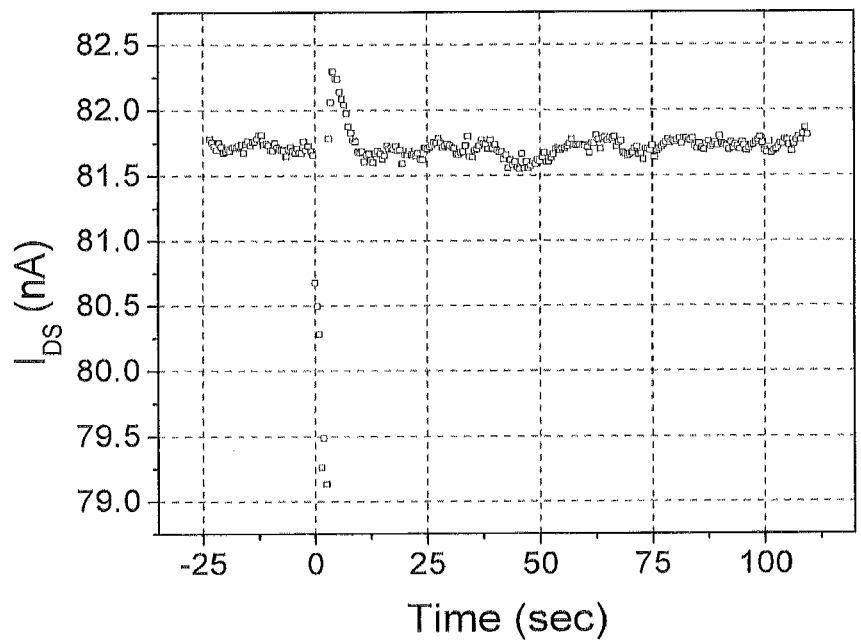
Figure 13E:
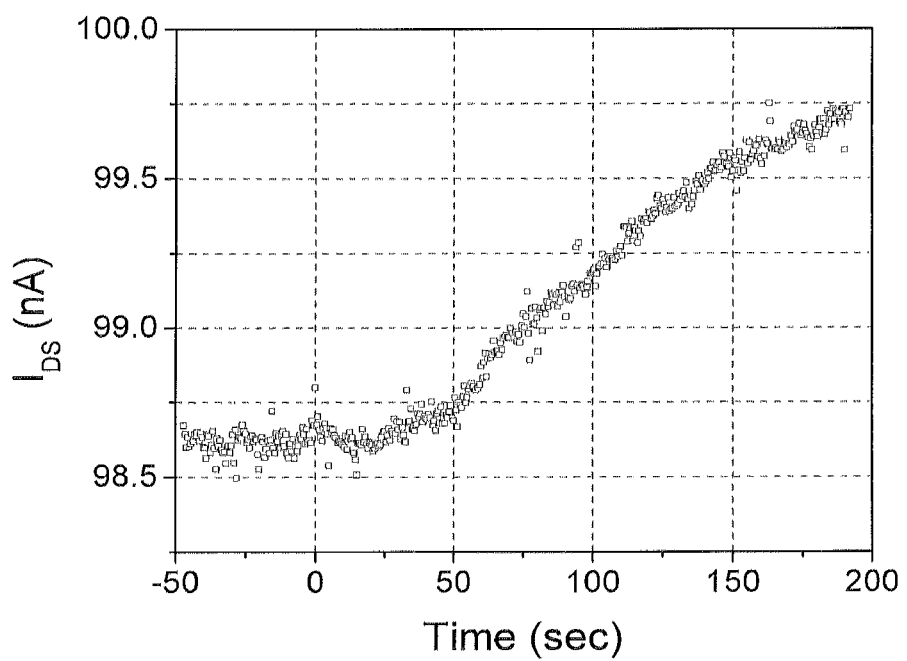
Figure 13F:
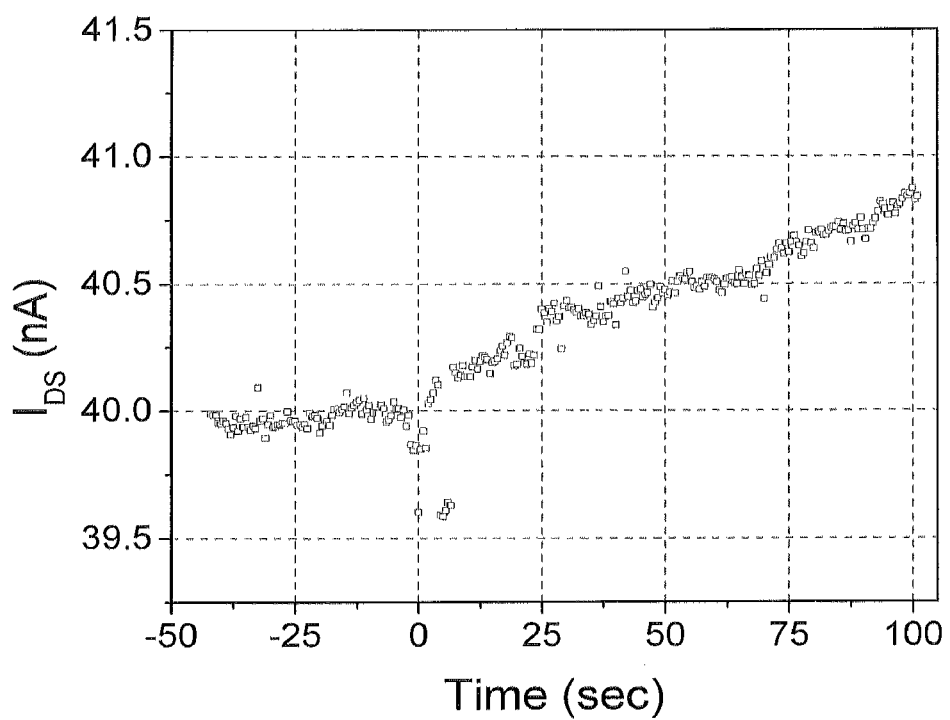
Figure 14A:
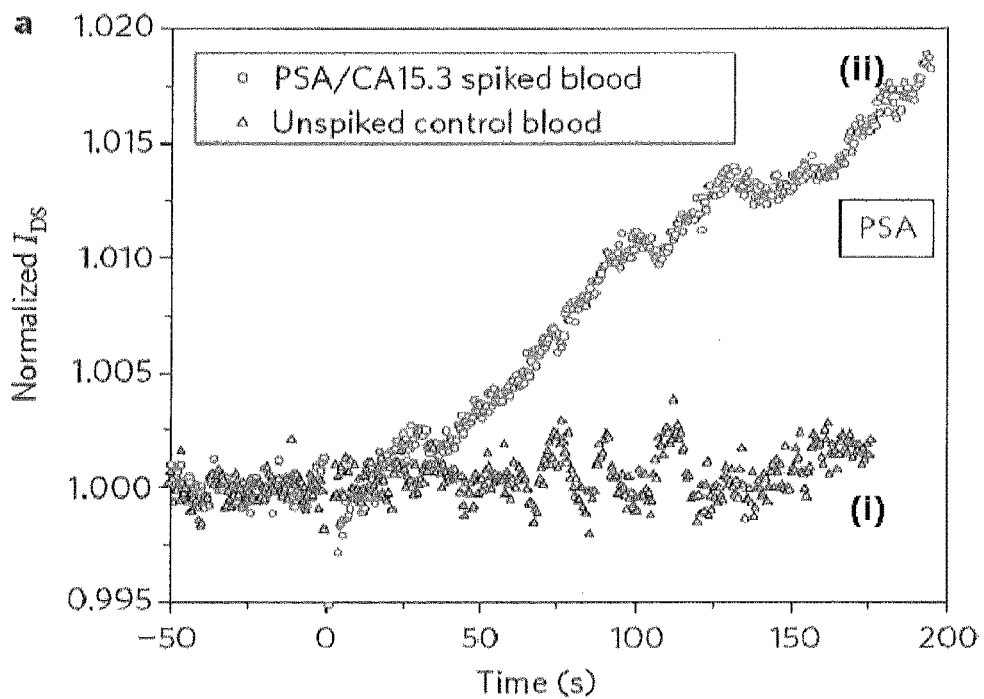
FIGS. 14A-14D, is a series of graphs illustrating sensing measurements using the label-free sensing. All sensing measurements were performed at $V_{DS}$=1V and $V_G$=−5V and all sample introductions occurred at time=0. Normalizations were performed by dividing device currents by the pre-addition (t<0) current level average. $V_{DS}$ corresponds to drain-source voltage.
Figure 14B:
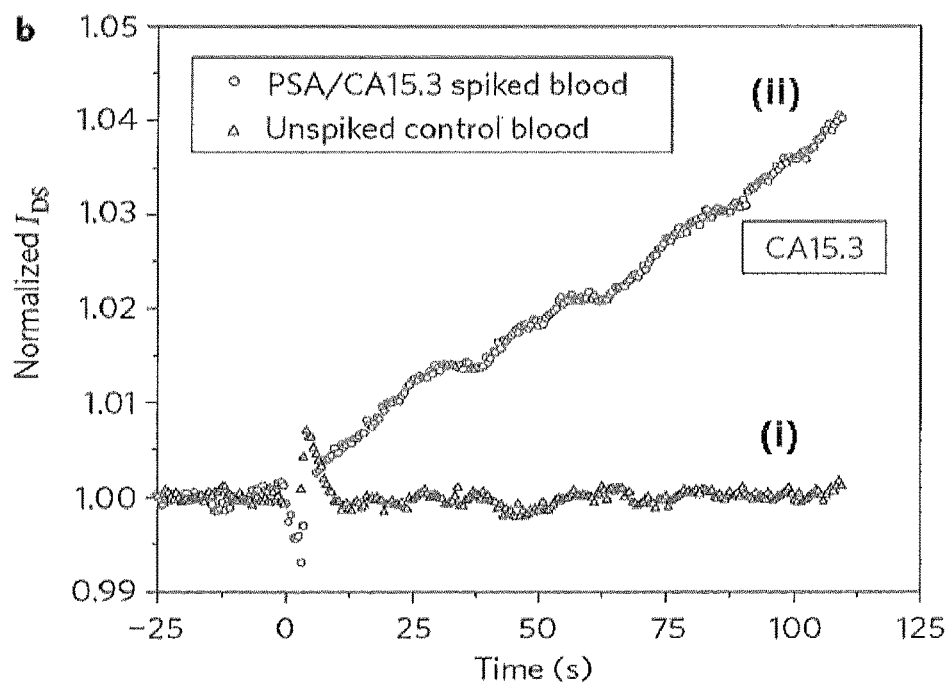
Figure 14C:
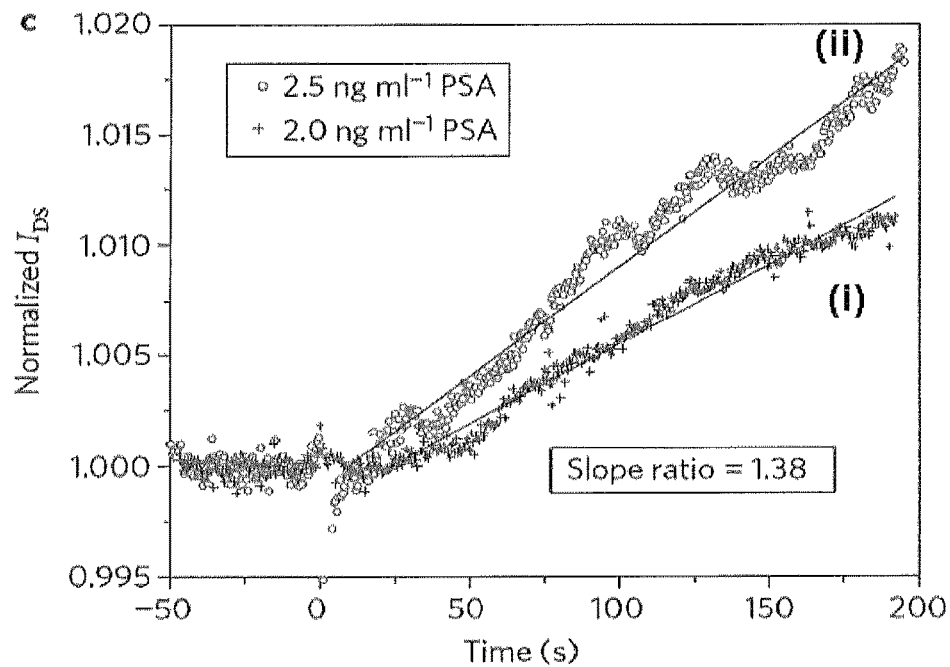
Figure 14D:
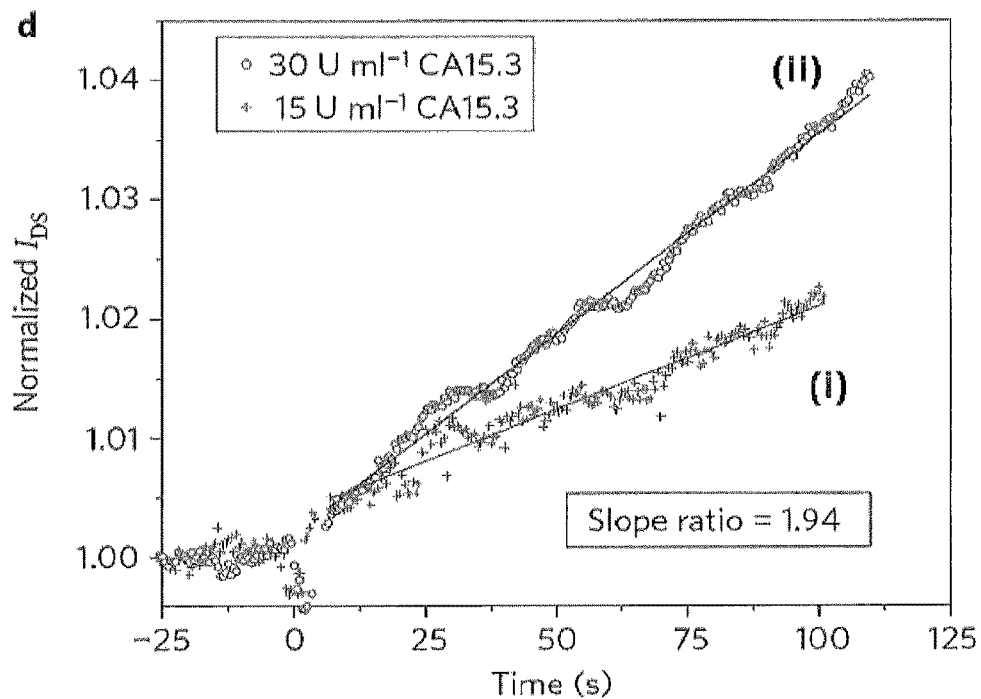

For FIGS. 14C and 14D, 5 µL of a microfluidic purification chip-purified, unspiked blood sample was added to anti-PSA and anti-CA15.3-functionalized devices, respectively. All heparinized blood samples used for sensing measurements were obtained from a Sprague Dawley rat. For the microfluidic purification chip-purified sensing experiments in FIGS. 14A and 14B, 5 µL of a microfluidic purification chip-purified, 2.5 ng/mL PSA- and 30 U/mL CA15.3-spiked blood sample was introduced to anti-PSA- and anti-CA15.3-functionalized devices. The absolute sensor responses are illustrated in FIGS. 13A and 13B, respectively. The absolute sensor responses for the unspiked control blood sample from FIGS. 14A-B are illustrated in FIGS. 13C and 13D for anti-PSA and anti-CA15.3 functionalized devices, respectively. The nanosensors responded similarly to the specific binding of antigens and antigen-antibody complexes. Although antigens from microfluidic purification chip-purified samples were complexed with the 20-mer conjugated first antibodies after UV irradiation (FIGS. 13E-F), these bound biomolecules trivially influenced nanosensor response, probably due to Debye screening-induced charge neutralization by the 1 mM bicarbonate buffer, selected to screen unbound proteins (Stern et al., 2007, Nano Lett. 7:3405).

For low-concentration measurements in FIG. 14C-D, a microfluidic purification chip-purified, 2.0 ng/mL PSA- and 15 U/mL CA15.3-spiked blood sample was introduced to anti-PSA- and anti-CA15.3-functionalized devices. The absolute sensor responses are given in FIGS. 13E and 13F, respectively.

Reproducibility of the measurement was assessed by measuring the same sample concentration with multiple distinct devices (between 7 to 10 devices), which gave for those concentrations a % error (standard) of <10%. Precision of the measurement was assessed by measuring different protein concentrations, and determining correlations of linear fits versus concentration. $R^2$ correlation coefficients of >0.97 were found for both PSA and CA15.3. Accuracy of the measurement was within the 10% reproducibility error.

Example 1

Derivatization of a Microfluidic Purification Chip.

The microfluidic purification chips were fabricated from 4-inch silicon wafers in a one-step photolithographic process (FIG. 4). A scanning electron micrograph of a completed, diced chip is shown in FIG. 3B. Modeling demonstrated that this geometry optimized binding (FIG. 3). Chip dimensions were selected such that the volume of the microfluidic purification chip (5 µL) was equivalent to about half the volume in the nanosensing reservoir, thus enabling complete transfer of microfluidic purification chip contents for sensing. The microfluidic purification chip surface area may maximally bind ~500 fmol of biomarker (assuming a 5 nm antibody hydrodynamic antibody radius). Complete release of bound complexes would therefore produce a ~100 nM biomarker solution, a value ~$10^6$ greater than that required for any type of sensing. The chip was thus suitable for simultaneous purification of multiple biomarkers.

The silicon oxide surface of the microfluidic purification chip was functionalized with 3-aminopropyltriethoxysilane (APTS) and avidin was bound using standard coupling chemistry, followed by fetal bovine serum (FBS) for blocking. Antibodies were conjugated through their carboxy termini to the commercially obtained biotinylated photocleavable crosslinkers, which contained a 20-mer DNA spacer (FIG. 3A). Upon photo induced cleavage, the antibody-DNA hybrid was removed from the surface and the DNA component was utilized for assay validation (FIG. 3C). Functionalized chips were loaded into a custom-machined flow chamber (FIG. 3B and FIG. 5), which enabled fluid handling and maintained a constant 5 µL volume in the system.

Example 2

Purification of Biomolecules Using Microfluidic Purification Chip.

Figure 3D:
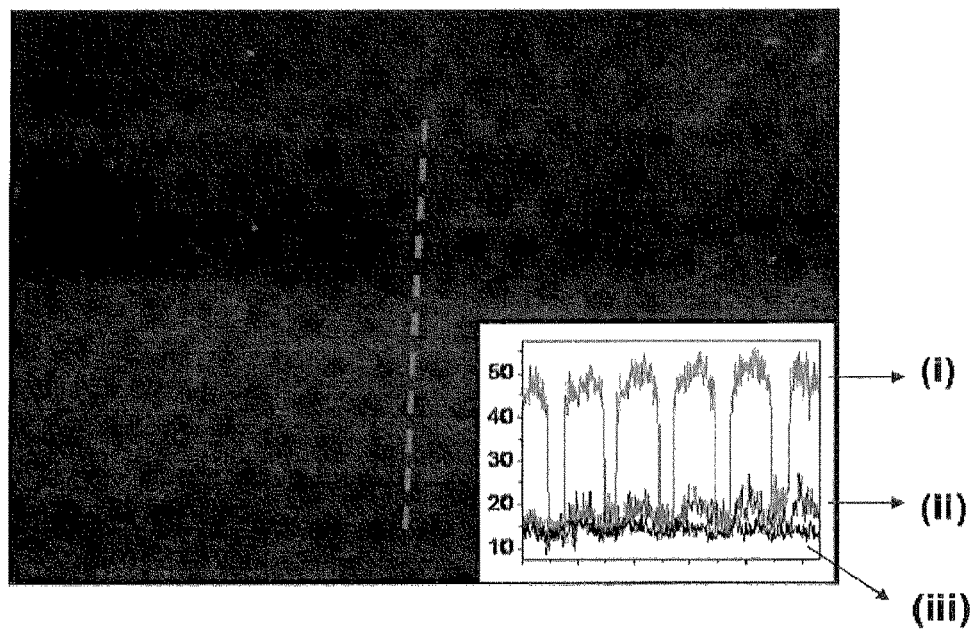

Microfluidic purification chip purification was demonstrated using anti-chicken ovatbumin (OVA) and a fluorescent protein conjugate, OVA-fluorescein-5-isothiocyanate (FITC), as illustrated in FIG. 3D. OVAFITC (10 ug/mL) was added to heparinized murine blood and flowed through the chip. After washing and flushing with sensing buffer, fluorescence imaging demonstrated specific OVAFITC binding to chip-bound antibodies (FIG. 3D). A control chip, to which anti-prostate specific antigen (PSA) was bound, showed a negligible fluorescent signal after a similarly spiked murine blood sample was flowed through the chip (inset, iii, FIG. 3D). After UV irradiation and subsequent flushing of the sensing reservoir with fresh buffer, the fluorescence signal from the anti-OVA chip was greatly diminished (inset, ii, FIG. 3D), validating successful binding and subsequent release of specific proteins with the microfluidic purification chip.

The generality of microfluidic purification chip purification operation was demonstrated using two model cancer antigens, PSA and carbohydrate antigen 15.3 (CA15.3). PSA is a standard clinical marker for prostate (Vickers et al., 2009, J. Clin. Oncol. 27:398-403; Shariat eta l., 2008, Can. J. Urol. 15:4363-4374). CA15.3 is a standard clinical marker for breast cancer (Rubach et al., 1997, Int. J. Biol. Markers 12:168-173; Uehara et al., 2008, Int. J. Clin. Oncol. 13:447-451). Nearly 100% of PSA and CA15.3 immunoreactivity was retained after UV irradiation (FIG. 6), demonstrating that the cleavage step did not compromise subsequent binding of complexes to nanosensor-bound second antibodies.

Successful capture and release of PSA and CA 15.3 was verified with a modified enzyme-linked immunoassay (ELISA) technique (FIG. 3C) that captured microfluidic purification chip-purified complexes to polystyrene plates with the same second antibodies used for sensing. The detection steps consisted of the hybridization of a complementary, biotinylated 20-mer to the crosslinker DNA sequence followed by streptavidin-horseradish peroxidase (HRP) binding and 3,3',5,5'-tetramethylbenzidine (TMB) addition. After 5-10 minutes, the reaction was terminated and absorbance was measured.

Six increasing concentrations of human PSA and CA15.3 were added to heparinized rat blood and samples were flowed through microfluidic purification chips functionalized with both anti-PSA and anti-CA 15.3. The introduced concentrations spanned the clinically relevant ranges, <2.4-6.5 ng/mL PSA and <18-25 U/mL CA 15.3 (Vickers et al., 2009, J. Clin. Oncol. 27:398-403; Shariat et al., 2008, Can. J. Urol. 15:4363-4374; Rubach et al., 1997, Int. J. Biol. Markers 12:168-173; Uehara et al., 2008, Int. J. Clin. Oncol. 13:447-451). Operation of microfluidic purification chips allowed for the successful simultaneous capture and release of PSA and CA 15.3, as respectively illustrated in FIGS. 3E and 3F. These data suggest that a monotonic relationship between the concentration of biomarker introduced in whole blood and that released into pure sensing buffer. Thus, appropriately calibrated devices should be capable of quantitative detection of biomarkers from physiologic samples. The absolute yields of these experiments, which were in the range of 5-10%, agreed with modeling studies (FIG. 2C) and were well below the upper limit for microfluidic purification chips. Biomarker capture by microfluidic purification chips may be significantly increased by adjusting either the operation conditions, such as the flow rate into the device (modeled in FIG. 2D), or the device dimensions or configuration, such as the inclusion of a recycle stream from the exit of the microfluidic purification chip.

Example 3

Characterization of Microfluidic Purification Chips Based on Nanoribbons.

Figure 3E:
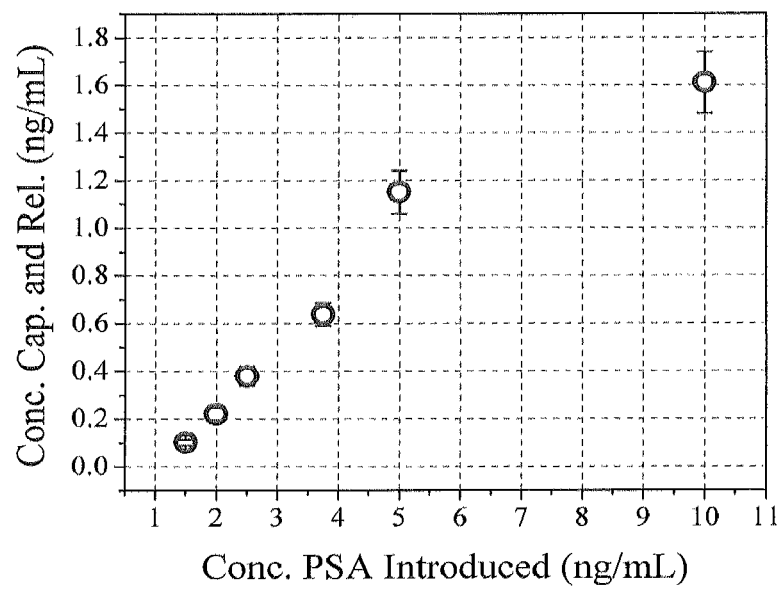
Figure 3F:
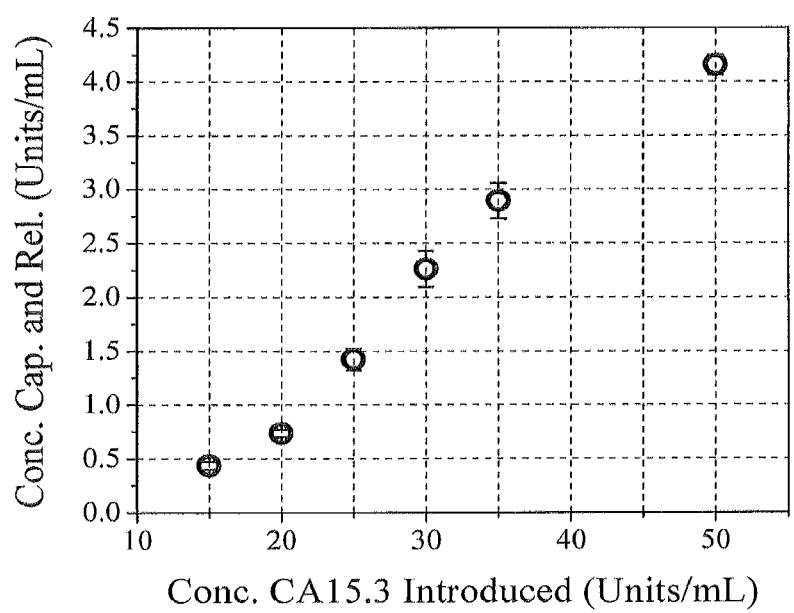

The integrated approach described in the previous examples allowed the microfluidic purification chip-purified biomarker complex concentrations to be well above those required for label-free, electronic detection. Previous studies using nanowire sensors have demonstrated PSA detection as low as 0.9 pg/mL (Zheng et al., 2005, Biotechnol. 23:1294-1301; Kim et al., 2007, Appl. Phys. Lett. 91:103901). That value is $10^3$-fold greater than sensitivities required for microfluidic purification chip-purified PSA detection (FIG. 3E).

The exquisite sensitivity of the PSA assay allowed the use of "nanoribbons," which are devices with nanoscale thicknesses and microscale lateral dimensions (Elfstrom et al., Nano Lett. 8:945-949). These devices are less sensitive but have significant fabrication and cost advantages. Fabricated from ultra-thin silicon-on-insulator (UT-SOI) wafers using conventional lithographic techniques, these devices have been demonstrated to detect streptavidin in the 0.0318-53 ng/mL range (Elfstrom et al., 2008, Nano Lett. 8:945-949), a sensitivity range ideally suited for microfluidic purification chip-purified cancer antigen detection.

25 nm-thin devices were prepared (FIG. 7), incorporating Ohmic contacts. An image of a sensor array and an optical micrograph of a completed device are illustrated in FIG. 9A, with the devices being 1 μm in width and having a 2 μm length exposed to the sensing solution through a passivating resist layer (FIG. 8).

Electrical characterization was performed to verify that this approach produced high-quality devices. Devices had on/off ratios of >10$^6$ (FIG. 9B) and the small hysteresis between forward and reverse $I_{DS}$(VG) sweeps suggested minimal defect-induced charge trapping (FIG. 9C). Surface functionalization did not compromise device electrical characteristics, with functionalized on/off ratios of >10$^4$ (FIG. 11). Solution gating using an exposed electrode in the sensing reservoir (FIG. 8C) to sweep the potential of the ionic solution ($V_{G,solv}$) demonstrated that device current ($I_{DS}$) levels were >100-fold larger than device-to-solution leakage current in the operating window for the device (−4 V≥$V_G$≥−15 V) and that the region of maximum device sensitivity was −2.5 V≥$V_G$≥−6 V (FIG. 8D). Devices were operated at $V_G$~5 V throughout sensing studies.

The 25 nm, Ohmically contacted nanoribbon sensors were capable of detecting sensing buffer spiked with PSA and CA15.3. The devices were functionalized either with anti-PSA or anti-CA15.3. Antibodies were immobilized to the sensor using N-hydroxysuccinimide (NHS)/1-ethyl-3-(3-dimethylaminopropyl)carbodiimide (EDC) chemistry. To verify that the signal from binding proteins would not be screened by the buffer solution, direct measurements of the amount of the signal that would be unscreened were carried out by varying buffer salt concentration. This study indicated that ~50% of the signal was not screened by the buffer solution. The normalized responses of anti-PSA and anti-CA15.3 functionalized devices to this solution are illustrated in FIGS. 14A and 14B, respectively, and demonstrate successful detection of these antigens. In comparison, null responses were observed when CA15.3-spiked buffer samples were added to PSA-specific devices and vice versa (FIG. 10). As observed in FIGS. 13A-B, after injection transient noise subsides, device current levels were increased by antigen binding due to the negative charge conferred to the antigens by the basic sensing buffer. The sensor signal increased throughout the course of the <200 sec measurements, suggesting that antigens continued to bind the sensor surface, as observed previously with similar devices for biotin-streptavidin sensing. The 25 nm nanoribbons thus appeared to meet the sensitivity and selectivity requirements for PSA and CA 15.3 detection.

Example 4

Analysis of Whole Blood Samples Using Microfluidic Purification Chips.

Experiments were performed to determine whether this integrated approach allows for direct electronic sensing from microfluidic purification chip-purified whole blood samples. The initial step was to verify whether unspiked, microfluidic purification chip-purified blood samples elicited any device response. After sample addition, neither PSA nor CA15.3 sensor current levels changed from their initial values for the duration of the measurements (FIGS. 14A-B, i). The normalized responses of these same devices to microfluidic purification chip-purified, antigen-spiked blood samples containing 2.5 ng/mL PSA and 30 U/mL CA15.3 are shown in FIGS. 14A and 14B (ii), respectively. After the injection transient noise subsided, device current levels were increased by antigen binding due to the negative charge conferred to the antigens by the basic sensing buffer. Similar signals were obtained with a PSA/CA15.3 spiked sensing buffer positive control, and no device response was observed with an unspiked, microfluidic purification chip-purified blood negative control. To reduce potential transient electrical signals upon injection, buffer salt concentrations of the functionalized devices and the microfluidic purification chip-purified samples were kept approximately the same. The positive signal was observed to increase linearly with time, following well-known ligand-receptor kinetics, in which initial rates at low relative analyte concentrations are directly proportional to species concentration. In fact, the asymptotic saturation value of the device response is weakly dependent on concentration for reversible reactions with a low dissociation constant, which is the case for the antigen-antibody interactions. Thus, the initial kinetic reaction rates were selected instead of endpoint detection.

After microfluidic purification chip purification, the concentrations matched those used for direct sensing buffer measurements (FIGS. 9E-F), thus similar device responses were anticipated. Indeed, similar signals were obtained, demonstrating effective, consistent, and integrated microfluidic purification chip operation. These data further indicated that the nanosensors responded similarly to the specific binding of antigens and antigen-antibody complexes. Although antigens from microfluidic purification chip-purified samples were complexed with the 20-mer conjugated first antibodies after UV irradiation (FIG. 3E-F), these bound biomolecules trivially influenced nanosensor response. This may have been caused by Debye screening-induced charge neutralization by the 1 mM bicarbonate buffer, which was selected to screen unbound proteins. Sensor responses to pure antigens and antigen-antibody complexes may be differentiated by decreasing the salt content of the buffer, providing a potential means for calibration.

Example 5

Quantitative Sensing Using Microfluidic Purification Chips.

Whole blood samples spiked with 2 ng/mL PSA and 15 U/mL CA 15.3 were microfluidic purification chip-purified and sensed with anti-PSA and anti-CA 15.3 functionalized devices. The normalized responses of these sensors are shown in FIGS. 14C-D. Using the slope of the normalized device temporal response, the slope ratios of both the PSA and CA15.3 responses agreed quite well with the initial spiked whole biomarker concentrations. For PSA, the slope ratio was 1.38, compared with a concentration ratio of 1.25. For CA15.3, the slope ratio was 1.94, compared with a concentration ratio of 2.0. This quantification occurred in the presence of another species, demonstrating selectivity.

Although the sensors were not calibrated for true quantitative detection, the data points indicated increased sensor responses for increased biomarker concentrations. As shown in other studies, the use of different devices did not obviate the use of these nanosensors for such measurements.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of pre-purifying and measuring the concentration of at least one biomarker in a physiological solution, wherein the method comprises the steps of:
contacting the physiological solution comprising the at least one biomarker with a microfluidic purification chip,
wherein the microfluidic purification chip comprises a first antibody directed to binding of a first epitope of the at least one biomarker, wherein the first antibody is attached to the microfluidic purification chip by a molecular crosslinker, wherein the first antibody is conjugated to the molecular crosslinker, and the molecular crosslinker is immobilized on the microfluidic purification chip,
wherein the molecular crosslinker comprises a molecular spacer and a cleavable group;
removing the physiological solution from the microfluidic purification chip;
optionally washing the microfluidic purification chip with a buffer;
cleaving the cleavable group in a sensing buffer to generate a biomarker-containing solution comprising complexes of the at least one biomarker bound to the first antibody;
transferring the biomarker-containing solution to a sensing chip, wherein the sensing chip comprises a nanowire sensor and the nanowire sensor is derivatized with a second antibody directed to binding of a second different epitope of the at least one biomarker of the complexes, wherein binding of the first antibody to the first epitope of the at least one biomarker does not prevent binding of the second antibody to the second epitope of the at least one biomarker;
contacting the biomarker-containing solution with the sensing chip wherein the second antibody binds the second epitope of the at least one biomarker, bound at the first epitope to the first antibody, of the complexes; and determining the concentration of the at least one biomarker, bound to the first antibody and the second antibody, in the biomarker-containing solution.

2. The method of claim 1, wherein the microfluidic purification chip is connected to the sensing chip by a duct, wherein the duct is used to transfer the biomarker-containing solution from the microfluidic purification chip to the sensing chip, the duct optionally comprising a valve.

3. The method of claim 1, wherein the sensing chip comprises a nanoribbon sensor.

4. The method of claim 1, wherein the sensing chip produces a gate voltage which ranges from about −2.5 V to about −6 V.

5. The method of claim 1, wherein the sensing solution has a Debye screening length of about $\lambda_D$=9.6 nm.

6. The method of claim 1, wherein the cleavable group is cleaved with UV or visible light or is cleaved with an acid, a base, an oxidant, or a reducer.

7. The method of claim 1, wherein the cleavable group of the molecular crosslinker is coupled to a biotin-containing moiety.

8. The method of claim 7, wherein the microfluidic purification chip is derivatized with avidin and the biotin-containing moiety of the molecular crosslinker is immobilized on the microfluidic purification chip via a binding interaction between the biotin-containing moiety and the avidin.

9. The method of claim 1, wherein the physiological solution is whole blood.

10. The method of claim 1, wherein the physiological solution comprises two or more biomarkers.

11. The method of claim 1, wherein the molecular spacer is selected from the group consisting of a peptide, a nucleic acid, a polyethylene glycol, and an alkylene group.

* * * * *